US009282915B2

(12) United States Patent
Carbonera et al.

(10) Patent No.: US 9,282,915 B2
(45) Date of Patent: Mar. 15, 2016

(54) METHOD AND SYSTEM FOR GENERATING AND/OR REPAIRING A SURFACE MODEL OF A GEOMETRIC STRUCTURE

(75) Inventors: Carlos Carbonera, Saint Paul, MN (US); Eric J. Voth, Maplewood, MN (US); Jeffrey A. Schweitzer, Saint Paul, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 1000 days.

(21) Appl. No.: 13/306,376

(22) Filed: Nov. 29, 2011

(65) Prior Publication Data

US 2013/0138404 A1    May 30, 2013

(51) Int. Cl.
| | |
|---|---|
| *G06F 7/60* | (2006.01) |
| *G06F 17/10* | (2006.01) |
| *A61B 5/107* | (2006.01) |
| *A61B 5/00* | (2006.01) |
| *A61B 5/042* | (2006.01) |
| *G06T 17/20* | (2006.01) |

(52) U.S. Cl.
CPC ............. *A61B 5/1076* (2013.01); *A61B 5/0044* (2013.01); *A61B 5/0053* (2013.01); *A61B 5/0422* (2013.01); *G06T 17/205* (2013.01); *G06T 2210/41* (2013.01); *G06T 2210/56* (2013.01)

(58) Field of Classification Search
CPC .................. G06T 17/00; G06T 17/20; G06T 2207/10028; G06T 19/00; G06T 19/20; G06T 2210/56; G06T 2210/41; G06T 2207/30004; G06T 2200/04; G06T 7/0051; G06T 15/00; G06T 7/0012; G06T 17/205; G06F 17/50; G06F 19/3437; A61B 5/1076; A61B 5/0422; A61B 5/0053; A61B 5/0044

USPC ............................... 703/1, 2, 6; 345/419, 420
See application file for complete search history.

(56) References Cited

U.S. PATENT DOCUMENTS

| | | | |
|---|---|---|---|
| 6,233,476 B1 | 5/2001 | Strommer et al. | |
| 6,301,496 B1 | 10/2001 | Reisfeld | |
| 6,377,865 B1 | 4/2002 | Edelsbrunner et al. | |

(Continued)

OTHER PUBLICATIONS

Attene et al., "ReMESH: An Interactive Environment to Edit and Repair Triangle Meshes," Shape Modeling and Applications, 2006. SMI 2006. IEEE Int'l Conference, Jun. 14-16, 2006, and Abstract corresponding to the same, 6 pages.

(Continued)

*Primary Examiner* — Dwin M Craig
(74) *Attorney, Agent, or Firm* — Dykema Gossett PLLC

(57) ABSTRACT

A method and system for generating and/or repairing surface models is provided. The method comprises acquiring data points corresponding to surface locations of a structure. The method further comprises generating a surface model of the structure based on the data points. The method further comprises adding additional data points to the point cloud formed by the acquired data points, and updating the model by constructing a surface model based on the added data points. The system comprises a processing apparatus configured to acquire data points corresponding to respective surface locations of a structure. The processing apparatus is further configured to generate a surface model of the structure based on the data points. The processing apparatus is further configured to add additional data points to the point cloud formed by the acquired data points, and update the surface model by constructing a surface model based on the added data points.

19 Claims, 20 Drawing Sheets

(56) References Cited

U.S. PATENT DOCUMENTS

| | | | |
|---|---|---|---|
| 6,498,944 | B1 | 12/2002 | Ben-Haim et al. |
| 6,690,963 | B2 | 2/2004 | Ben-Haim et al. |
| 6,788,967 | B2 | 9/2004 | Ben-Haim et al. |
| 7,197,354 | B2 | 3/2007 | Sobe |
| 7,263,397 | B2 | 8/2007 | Hauck et al. |
| 7,386,339 | B2 | 6/2008 | Strommer et al. |
| 7,536,218 | B2 | 5/2009 | Govari et al. |
| 7,825,925 | B2 | 11/2010 | Voth |
| 7,988,639 | B2 * | 8/2011 | Starks .................. A61B 5/0402 600/424 |
| 2004/0254437 | A1 * | 12/2004 | Hauck et al. .................. 600/374 |
| 2005/0018901 | A1 * | 1/2005 | Kaufmann .............. G06T 17/20 382/154 |
| 2006/0116838 | A1 * | 6/2006 | Chang et al. ..................... 702/98 |
| 2007/0073179 | A1 | 3/2007 | Afonso et al. |
| 2007/0270705 | A1 * | 11/2007 | Starks ........................... 600/523 |
| 2009/0167755 | A1 * | 7/2009 | Voth .............................. 345/419 |
| 2009/0171627 | A1 | 7/2009 | Olson |
| 2009/0262109 | A1 | 10/2009 | Markowitz |
| 2010/0168620 | A1 | 7/2010 | Klimovitch et al. |
| 2010/0274123 | A1 | 10/2010 | Voth |

OTHER PUBLICATIONS

Barequet et al., "RSVP: A Geometric Toolkit for Controlled Repair of Solid Models," IEEE Transactions on Visualization and Computer Graphics, vol. 4, No. 2, Apr.-Jun. 1998, 16 pages.

Barequet et al., "Filling Gaps in the Boundary of a Polyhedron," Computer Aided Geometric Design, vol. 12, No. 2, pp. 207-229(23) Mar. 1995, and Abstract corresponding to the same.

Carr et al., "Surface Interpolation with Radial Basis Functions for Medical Imaging," IEEE Transactions on Medical Imaging, vol. 16, No. 1, Feb. 1997, 12 pages.

Ju, T. "Fixing Geometric Errors on Polygonal Models: A Survey," Journal of Computer Science and Technology, vol. 24, No. 1, pp. 19-29, Jan. 2009.

Ju, T. "Robust Repair of Polygonal Models," ACM Transactions on Graphics (TOG)—Proceedings of ACM SIGGRAPH 2004, vol. 23, Issue 3, Aug. 2004, and Abstract corresponding to the same, 8 pages.

Hornung et al., "Robust Reconstruction of Watertight 3D Models from Non-Uniformly Sampled Point Clouds Without Normal Information," Eurographics Symposium on Geometry Processing (2006), 10 pages.

International Search Report and Written Opinion in PCT Application No. PCT/US2012/026767 (Jun. 6, 2012).

Ebeida, Mohamed S. et al., "Isotropic conforming refinement of quadrilateral and hexahedral meshes using two-refinement templates", International Journal for Numerical Methods in Engineering, vol. 88, No. 10, pp. 974-985, May 3, 2011.

Guo, Baining et al., "surface reconstruction using alpha shapes", Computer Graphics Forum, vol. 16, No. 4, pp. 177-190, Oct. 1, 1997.

Li, Xiangrong et al., "3D mesh adaptation by mesh modification", Computer methods in applied mechanics and engineering, North-Holland, Amsterdam, NL, vol. 194, No. 48-49, pp. 4915-4950, Nov. 15, 2005.

Supplementary European Search Report in EP Application No. 12584171.1 (Apr. 24, 2015).

Yin, ZhouPing et al., "Defective point data reconstruction based on improved process of morphological operations", Science China Technological Sciences, vol. 54, No. 12, pp. 3166-3179, Dec. 2011.

* cited by examiner

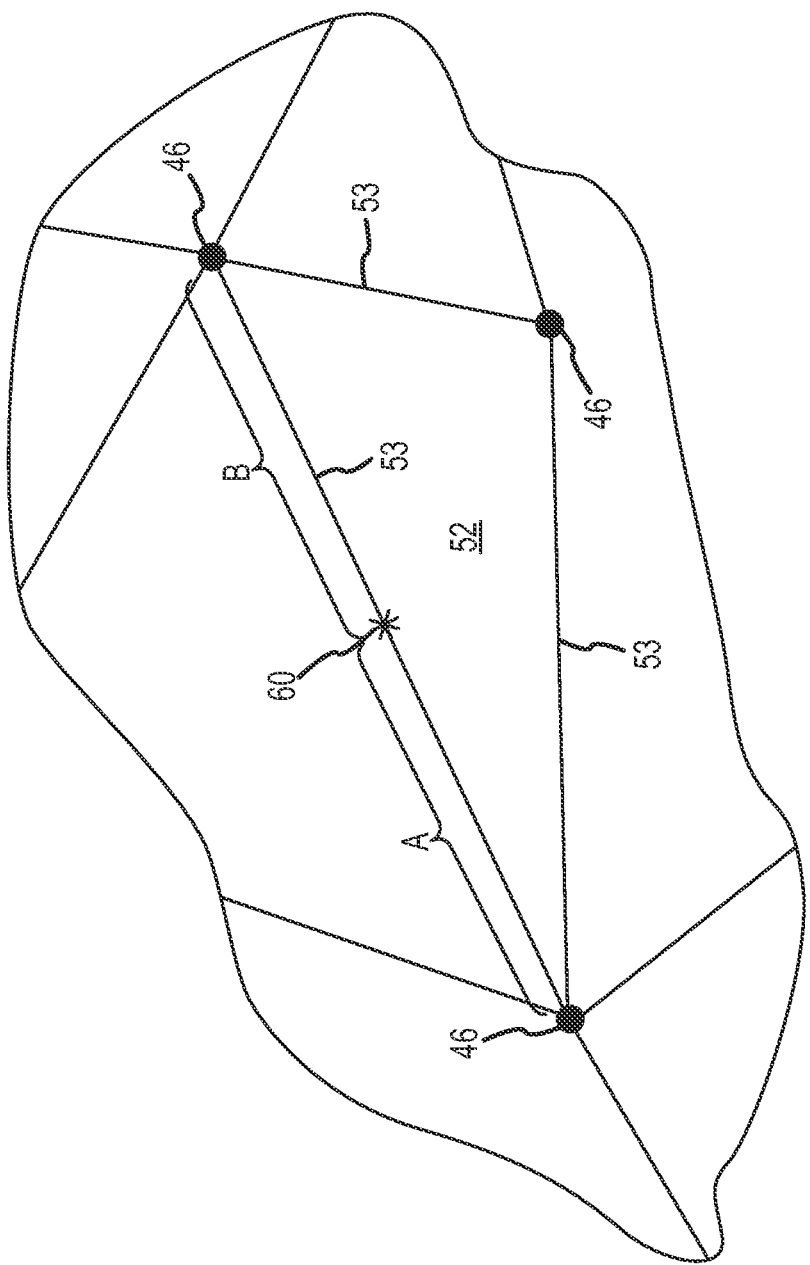

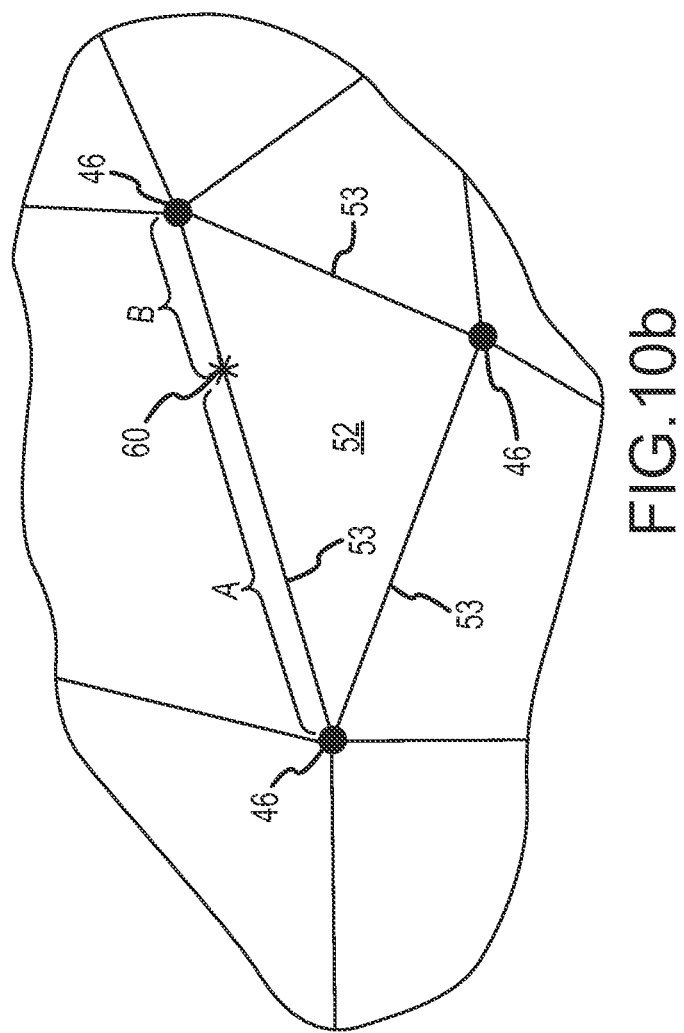

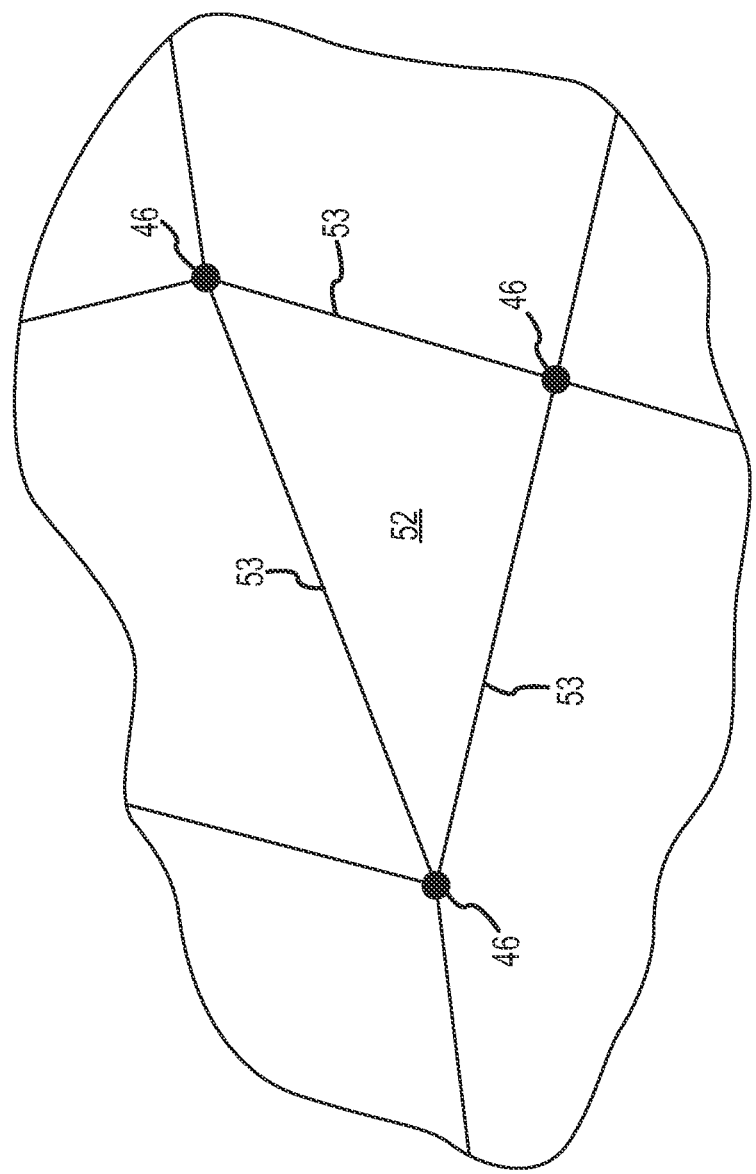

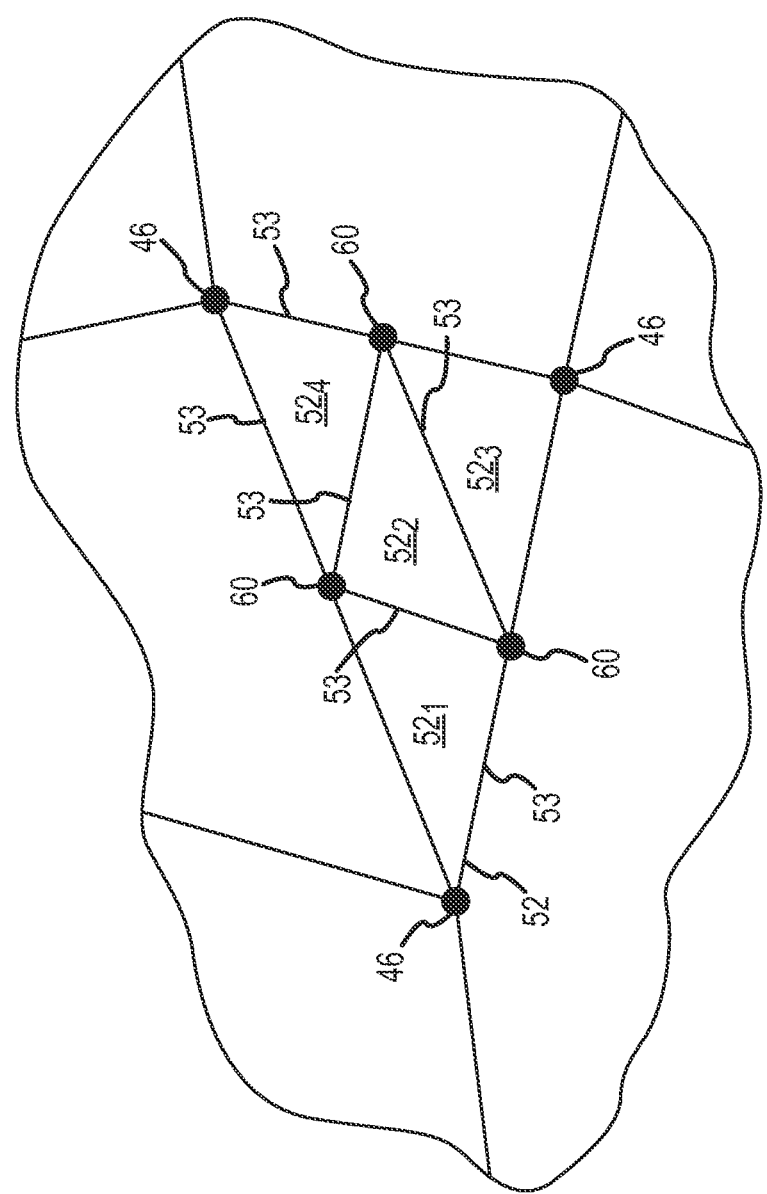

METHOD AND SYSTEM FOR GENERATING AND/OR REPAIRING A SURFACE MODEL OF A GEOMETRIC STRUCTURE

BACKGROUND OF THE INVENTION a. Field of the Invention

This disclosure relates to a system and method for generating and/or repairing a surface model of a geometric structure. More particularly, this disclosure relates to a computer-implemented system and method for generating and/or repairing a surface model of an anatomic structure, such as, for example, the heart or a particular portion thereof, using location data points.

b. Background Art

It is known that various computer-implemented systems and methodologies can be used to generate surface models of geometric structures, such as, for example, anatomic structures. More specifically, a variety of systems and methods have been used to generate surface models of the heart and/or particular portions thereof.

One conventional methodology or technique involves the use of one of a number of known alpha shape algorithms to compute an alpha shell based on a plurality of location data points corresponding to respective locations on the surface of the geometric structure. More particularly, but in general terms, a plurality of location data points are collected from the surface of the geometric structure to form a point cloud. An alpha shape algorithm is then applied to the point cloud to compute an alpha shell of the point cloud, which results in the generation of a surface model of the geometric structure. Such a technique results in a mesh surface model of the geometric structure comprising a plurality of triangularly-shaped facets, each of which is defined, in part, by three location data points that serve as the vertices of one or more facets.

While surface models generated using the alpha shape technique have proved useful and desirable in applications such as, for example, electrophysiological mapping, the technique is not without its disadvantages. For example, a surface model generated using the alpha shape technique is considered to be closed and "manifold" if each edge of the alpha shell is shared by exactly two facets and each vertex (i.e., location data point) is shared by facets that make a single ordered loop around that vertex. However, in certain instances, alpha shells tend to have defects such as, for example, missing facets, non-manifold vertices, and holes that cannot be filled in a way that renders the final alpha shell, and therefore, surface model, manifold. Thus, while the alpha shape technique provides advantages over other conventional surface model generating techniques/methodologies, and generally produces surface models that have a relatively high degree of detail, they do not always provide surface models having a desirable level of completeness or accuracy.

Accordingly, the inventors herein have recognized a need for a system and method for generating and/or repairing surface models of geometric structures that will minimize and/or eliminate one or more of the deficiencies in conventional systems.

BRIEF SUMMARY OF THE INVENTION

The present invention is directed to a system and method for generating and/or repairing surface models of geometric structures. In accordance with one aspect of the invention and the present teachings, a method of generating a surface model of a geometric structure comprises a step of acquiring a plurality of location data points corresponding to respective locations on the surface of the geometric structure, wherein the plurality of location data points forms a point cloud. The method further comprises a step of generating a first surface model of the geometric structure based on the plurality of location data points in the point cloud. In an exemplary embodiment, the first surface model is generated by computing an alpha shell of the point cloud using an alpha shape algorithm. The method still further comprises a step of adding a plurality of additional data points to the point cloud, and a step of updating the first surface model by constructing a second surface model based on the plurality of added data points. In an exemplary embodiment, the adding step comprises adding a plurality of additional data points wherein each of the additional data points is disposed a distance from at least one of the plurality of location data points that is substantially equal to a radius of a catheter used to collect the plurality of location data points. In an exemplary embodiment, the second surface model is constructed by computing an alpha shell of the added data points using an alpha shape algorithm.

In accordance with another aspect of the invention, a system for generating a surface model of a geometric structure is provided. In accordance with the present teachings, the system comprises a processing apparatus configured to acquire a plurality of location data points corresponding to respective locations on the surface of said geometric structure, wherein the plurality of location data points forms a point cloud. The processing apparatus is further configured to generate a first surface model of the geometric structure based on the plurality of location data points in the point cloud. The processing apparatus is still further configured to add a plurality of additional data points to the point cloud, and to update the first surface model by constructing a second surface model based on the plurality of added data points In accordance with yet another aspect of the invention, a method of repairing a surface model of a geometric structure is provided. In accordance with the present teachings, the method includes a step of acquiring the surface model of the geometric structure. In an exemplary embodiment, the surface model is based on a plurality of location data points corresponding to respective locations on the surface of the geometric structure, and the location data points collectively form a point cloud. The method further comprises a step of adding a plurality of additional data points to the point cloud. The method still further comprises a step of updating the surface model by constructing a second surface model based on the plurality of added data points. In an exemplary embodiment, the second surface model is constructed by computing an alpha shell of the added data points using an alpha shape algorithm.

The foregoing and other aspects, features, details, utilities, and advantages of the present invention will be apparent from reading the following description and claims, and from reviewing the accompanying drawings.

BRIEF DESCRIPTION OF THE DRAWINGS

FIGS. 10a-10c are enlarged views of portions of a three-dimensional alpha shell depicting triangularly-shaped facets thereof and illustrating another exemplary data point adding technique wherein an edge of a facet is segmented and refined data points are added thereto.

FIGS. 11a-11c are enlarged views of a portion of a three-dimensional alpha shell depicting triangularly-shaped facets thereof and illustrating yet another exemplary data point adding technique wherein refined data points are added to the edges of a facet and the facet is broken into a plurality of new facets.

DETAILED DESCRIPTION OF EMBODIMENTS OF THE INVENTION

Figure 1:
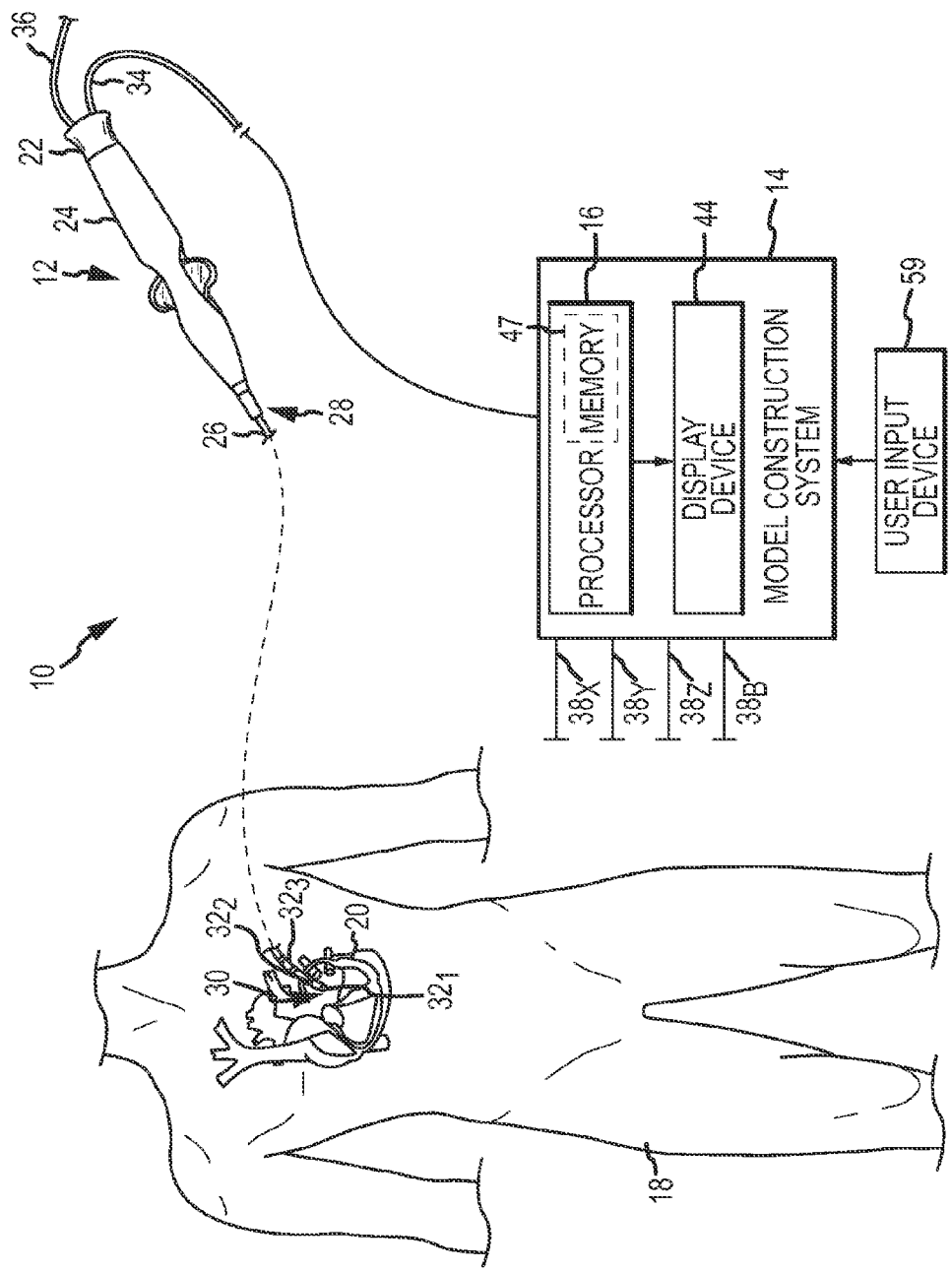
FIG. 1 is a diagrammatic view of a system for generating and/or repairing a surface model of a geometric structure in accordance with the present teachings.

Referring now to the drawings wherein like reference numerals are used to identify identical components in the various views, FIG. 1 illustrates one exemplary embodiment of a system 10 for generating and/or repairing surface models of geometric structures. It should be noted that while the following description focuses primarily on the use of the system 10 in the generation and repair of surface models of anatomic structures, and cardiac structures, in particular, the present disclosure is not meant to be so limited. Rather, the system 10, and the methods and techniques used thereby, may be applied to the generation of surface models of any number of geometric structures, including anatomic structures other than those of the heart. However, for illustrative and ease of description purposes, the description below will be limited to the use of system 10 in the generation of cardiac surface models.

With continued reference to FIG. 1, in an exemplary embodiment, the system 10 comprises, among other components, a medical device 12, such as, for example, a catheter (catheter 12), and a model construction system 14 comprising, in part, a processing apparatus 16, such as, for example, an electronic control unit, that is configured to construct a surface model of structures within the heart using data collected by the catheter 12.

As illustrated in FIG. 1, the catheter 12 is configured to be inserted into a patient's body 18, and more particularly, into the patient's heart 20. The catheter 12 may include a cable connector or interface 22, a handle 24, a shaft 26 having a proximal end 28 and a distal end 30 (as used herein, "proximal" refers to a direction toward the end of the catheter 12 near the clinician, and "distal" refers to a direction away from the clinician and (generally) inside the body of a patient), and one or more sensors 32 (e.g., $32_1$, $32_2$, $32_3$) mounted in or on the shaft 26 of the catheter 12. In an exemplary embodiment, the sensors 32 are disposed at or near the distal end 30 of the shaft 26. The catheter 12 may further include other conventional components such as, for example and without limitation, a temperature sensor, additional sensors or electrodes, ablation elements (e.g., ablation tip electrodes for delivering RF ablative energy, high intensity focused ultrasound ablation elements, etc.), and corresponding conductors or leads.

The connector 22 provides mechanical, fluid, and electrical connection(s) for cables, such as, for example, cables 34, 36 extending to the model construction system 14 and/or other components of the system 10 (e.g., a visualization, navigation, and/or mapping system (if separate and distinct from the model construction system 14), an ablation generator, irrigation source, etc.). The connector 22 is conventional in the art and is disposed at the proximal end of the catheter 12, and the handle 24 thereof, in particular.

The handle 24, which is disposed at the proximal end 28 of the shaft 26, provides a location for the clinician to hold the catheter 12 and may further provide means for steering or guiding the shaft 26 within the body 18 of a patient. For example, the handle 24 may include means to change the length of a steering wire extending through the catheter 12 to the distal end 30 of the shaft 26 to steer the shaft 26. The handle 24 is also conventional in the art and it will be understood that the construction of the handle 24 may vary. In another exemplary embodiment, the catheter 12 may be robotically driven or controlled. Accordingly, rather than a clinician manipulating a handle to steer or guide the catheter 12, and the shaft 26 thereof, in particular, in such an embodiment a robot is used to manipulate the catheter 12.

The shaft 26 is an elongate, tubular, flexible member configured for movement within the body 18. The shaft 26 supports, for example and without limitation, sensors and/or electrodes mounted thereon, such as, for example, the sensors 32, associated conductors, and possibly additional electronics used for signal processing and conditioning. The shaft 26 may also permit transport, delivery, and/or removal of fluids (including irrigation fluids, cryogenic ablation fluids, and bodily fluids), medicines, and/or surgical tools or instruments. The shaft 26 may be made from conventional materials such as polyurethane, and defines one or more lumens configured to house and/or transport electrical conductors, fluids, or surgical tools. The shaft 26 may be introduced into a blood vessel or other structure within the body 18 through a conventional introducer. The shaft 26 may then be steered or guided through the body 18 to a desired location, such as the heart 20, using means well known in the art.

The sensors 32 mounted in or on the shaft 26 of the catheter 12 may be provided for a variety of diagnostic and therapeutic purposes including, for example and without limitation, electrophysiological studies, pacing, cardiac mapping, and ablation. In an exemplary embodiment, one or more of the sensors 32 are provided to perform a location or position sensing function. More particularly, and as will be described in greater detail below, one or more of the sensors 32 are configured to be a positioning sensor(s) that provide information relating to the location (position and orientation) of the catheter 12, and the distal end 30 of the shaft 26 thereof, in particular, at certain points in time. Accordingly, in such an embodiment, as the catheter 12 is moved along a surface of a desired structure of the heart 20, the sensor(s) 32 can be used to collect location data points that correspond to the surface of the desired structure. These location data points can then be used by, for example, the model construction system 14, to construct a surface model of the desired structure, which will be described in greater detail below. For purposes of clarity and illustration, the description below will be limited to an embodiment wherein each of the sensors 32 of the catheter 12 comprise positioning sensors. It will be appreciated, however, that in other exemplary embodiments, which remain within the spirit and scope of the present disclosure, the catheter 12 may comprise both positioning sensors and other sensors configured to perform other diagnostic and/or therapeutic functions.

As briefly described above, the model construction system 14 is configured to construct a surface model of structures within the heart using location data collected by the catheter 12. More particularly, the processing apparatus 16 of the model construction system 14 is configured to acquire location data points collected by the sensor(s) 32 and to then construct a surface model of the structure to which the location data points correspond. In an exemplary embodiment, the model construction system 14 acquires the location data points by functioning with the sensors 32 to collect location data points. In another exemplary embodiment, however, the model construction system 14 may simply acquire the location data points from the sensors 32 or another component in the system 10 without affirmatively taking part in the collection of the location data points. In either embodiment, the model construction system 14 is configured to construct a surface model based on some or all of the collected location data points. For purposes of illustration and clarity, the description below will be limited to an embodiment wherein the model construction system 14 is configured to both construct the surface model and also acquire location data points by functioning with the sensor(s) 32 in the collection of the location data points. It will be appreciated, however, that embodiments wherein the model construction system 14 only acquires location data points from the sensor(s) 32 or another component of the system 10 and then constructs a surface model based thereon remain within the spirit and scope of the present disclosure.

Accordingly, in an exemplary embodiment, in addition to constructing a surface model of a structure, the model construction system 14 is configured to function with the sensor(s) 32 to collect location data points that are used in the construction of a surface model. In such an embodiment, the model construction system 14 may comprise an electric field-based system, such as, for example, the EnSite NavX™ system commercially available from St. Jude Medical, Inc., and generally shown with reference to U.S. Pat. No. 7,263,397 entitled "Method and Apparatus for Catheter Navigation and Location and Mapping in the Heart", the entire disclosure of which is incorporated herein by reference. In other exemplary embodiments, however, the model construction system 14 may comprise other types of systems, such as, for example and without limitation: a magnetic-field based system such as the Carto™ System available from Biosense Webster, and as generally shown with reference to one or more of U.S. Pat. Nos. 6,498,944 entitled "Intrabody Measurement," 6,788,967 entitled "Medical Diagnosis, Treatment and Imaging Systems," and 6,690,963 entitled "System and Method for Determining the Location and Orientation of an Invasive Medical Instrument," the entire disclosures of which are incorporated herein by reference, or the gMPS system from MediGuide Ltd., and as generally shown with reference to one or more of U.S. Pat. Nos. 6,233,476 entitled "Medical Positioning System," 7,197,354 entitled "System for Determining the Position and Orientation of a Catheter," and 7,386,339 entitled "Medical Imaging and Navigation System," the entire disclosures of which are incorporated herein by reference; a combination electric field-based and magnetic field-based system such as the Carto 3™ System also available from Biosense Webster, and as generally shown with reference to U.S. Pat. No. 7,536,218 entitled "Hybrid Magnetic-Based and Impedance-Based Position Sensing," the entire disclosure of which is incorporated herein by reference; as well as other impedance-based localization systems, acoustic or ultrasound-based systems, and commonly available fluoroscopic, computed tomography (CT), and magnetic resonance imaging (MRI)-based systems.

As briefly described above, the sensor(s) 32 of the catheter 12 comprise positioning sensors. The sensor(s) 32 produce signals indicative of catheter location (position and/or orientation) information. In an embodiment wherein the model construction system 14 is an electric field-based system, the sensor(s) 32 may comprise one or more electrodes. Alternatively, in an embodiment wherein the model construction system 14 is a magnetic field-based system, the sensor(s) 32 may comprise one or more magnetic sensors configured to detect one or more characteristics of a low-strength magnetic field. For instance, in one exemplary embodiment, the sensor(s) 32 may comprise magnetic coils disposed on or in the shaft 26 of the catheter 12.

For purposes of clarity and illustration, the model construction system 14 will hereinafter be described as comprising an electric field-based system, such as, for example, the EnSite NavX™ system identified above. It will be appreciated that while the description below is primarily limited to an embodiment wherein the sensor(s) 32 comprise one or more electrodes, in other exemplary embodiments, the sensor(s) 32 may comprise one or more magnetic field sensors (e.g., coils). Accordingly, model construction systems that include positioning sensor(s) other than the sensors or electrodes described below remain within the spirit and scope of the present disclosure.

Figure 2:
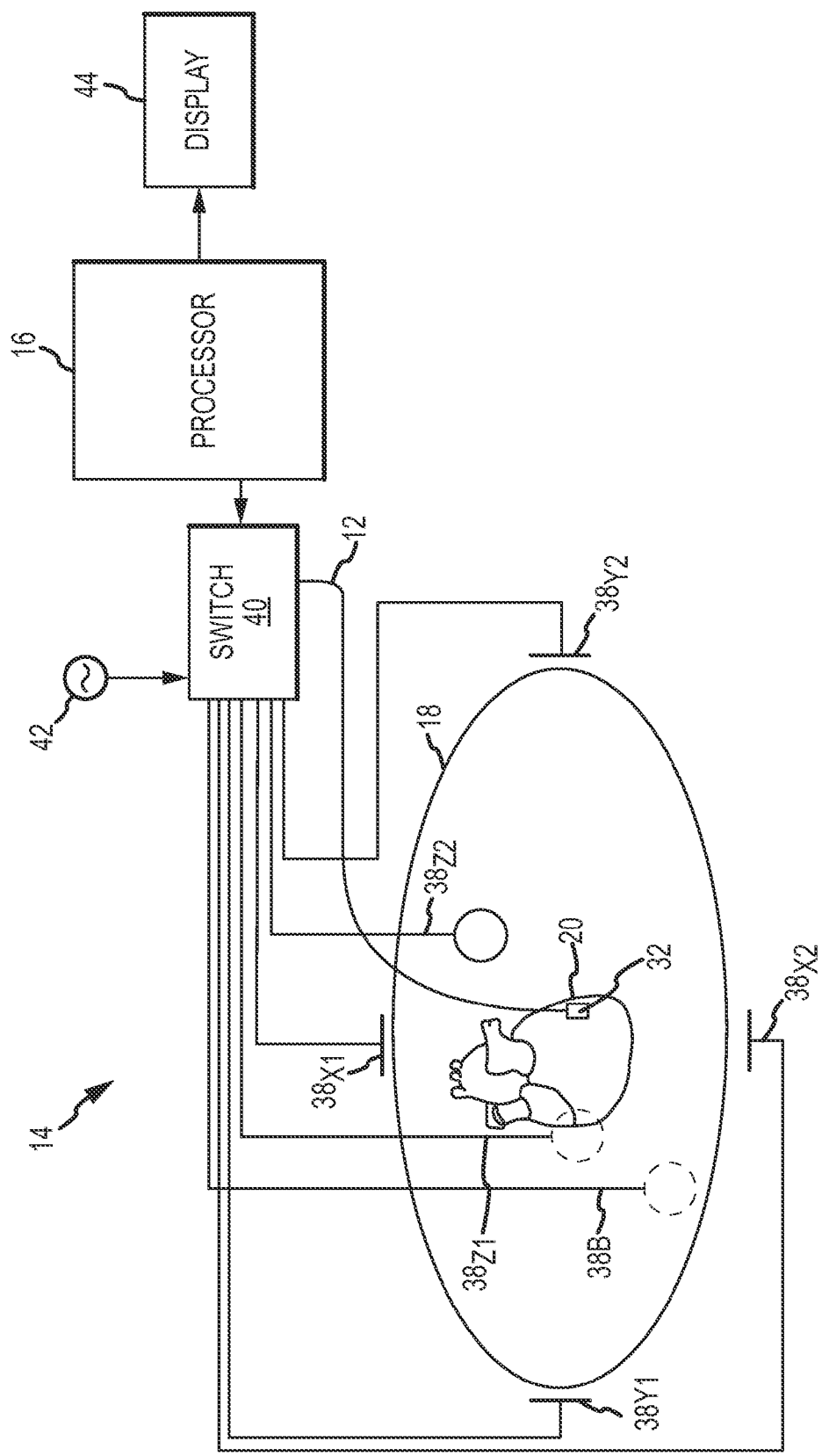
FIG. 2 is a simplified diagrammatic and schematic view of the model construction system of the system illustrated in FIG. 1.

With reference to FIG. 2, in addition to the processing apparatus 16, the model construction system 14 may include, among other possible components, a plurality of patch electrodes 38, a multiplex switch 40, a signal generator 42, and a display device 44. In another exemplary embodiment, some or all of these components are separate and distinct components that are electrically connected to, and configured for communication with, the model construction system 14.

The processing apparatus 16 may comprise a programmable microprocessor or microcontroller, or may comprise an application specific integrated circuit (ASIC). The processing apparatus 16 may include a central processing unit (CPU) and an input/output (I/O) interface through which the processing apparatus 16 may receive a plurality of input signals including, for example, signals generated by patch electrodes 38 and the sensor(s) 32, and generate a plurality of output signals including, for example, those used to control and/or provide data to, for example, the display device 44 and the switch 40. The processing apparatus 16 may be configured to perform various functions, such as those described in greater detail above and below, with appropriate programming instructions or code (i.e., software). Accordingly, the processing apparatus 16 is programmed with one or more computer programs encoded on a computer storage medium for performing the functionality described herein.

With the exception of the patch electrode $38_B$ called a "belly patch," the patch electrodes 38 are provided to generate electrical signals used, for example, in determining the position and orientation of the catheter 12. In one embodiment, the patch electrodes 38 are placed orthogonally on the surface of the body 18 and are used to create axes-specific electric fields within the body 18. For instance, in one exemplary embodiment, patch electrodes $38_{X1}$, $38_{X2}$ may be placed along a first (x) axis. Patch electrodes $38_{Y1}$, $38_{Y2}$ may be placed along a second (y) axis, and patch electrodes $38_{Z1}$, $38_{Z2}$ may be placed along a third (z) axis. Each of the patch electrodes 38 may be coupled to the multiplex switch 40. In an exemplary embodiment, the processing apparatus 16 is configured, through appropriate software, to provide control signals to the switch 40 to thereby sequentially couple pairs of electrodes 38 to the signal generator 42. Excitation of each pair of electrodes 38 generates an electric field within body 18 and within an area of interest such as the heart 20. Voltage levels at non-excited electrodes 38, which are referenced to the belly patch $38_B$, are filtered and converted and provided to processing apparatus 16 for use as reference values.

In an exemplary embodiment, the sensor(s) 32 of the catheter 12 are electrically coupled to the processing apparatus 16 and are configured to serve a position sensing function. More particularly, the sensor(s) 32 are placed within electric fields created in the body 18 (e.g., within the heart) by exciting the patch electrodes 38. For purposes of clarity and illustration only, the description below will be limited to an embodiment wherein a single sensor 32 is placed within the electric fields. It will be appreciated, however, that in other exemplary embodiments that remain within the spirit and scope of the present disclosure, a plurality of sensors 32 can be placed within the electric fields and then positions and orientations of each sensor can be determined using the techniques described below.

Figure 3:
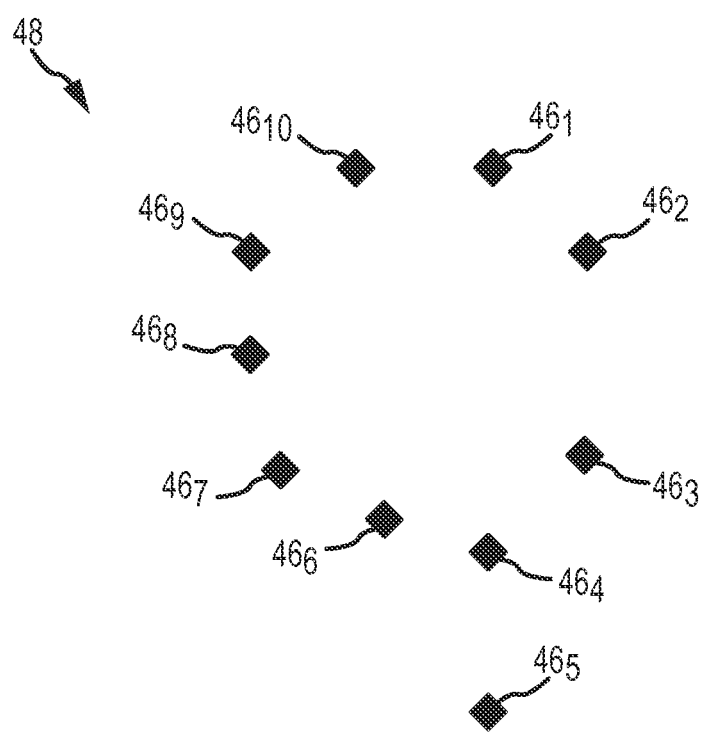
FIG. 3 is a schematic view of a point cloud containing a collection of location data points.
Figure 4A:
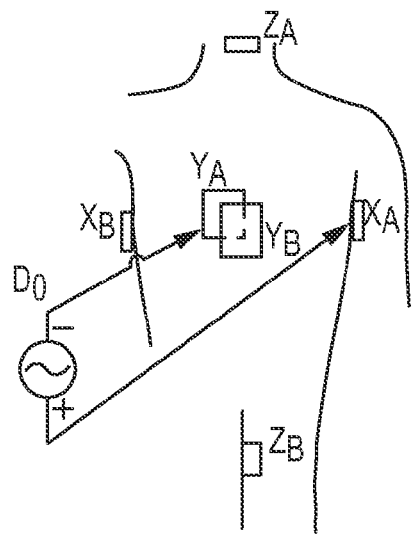
FIGS. 4a-4d are schematic diagrams of exemplary dipole pairs of driven patch electrodes suitable for use in the model construction system illustrated in FIG. 2.
Figure 4B:
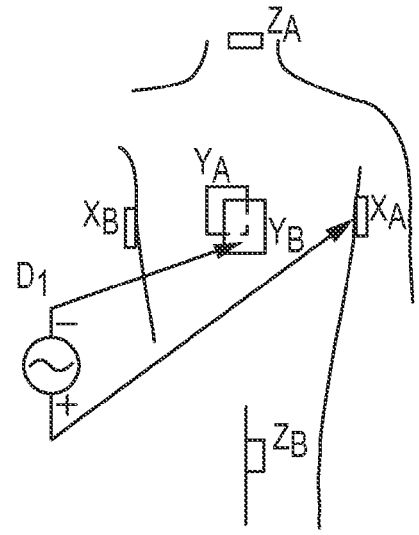
Figure 4C:
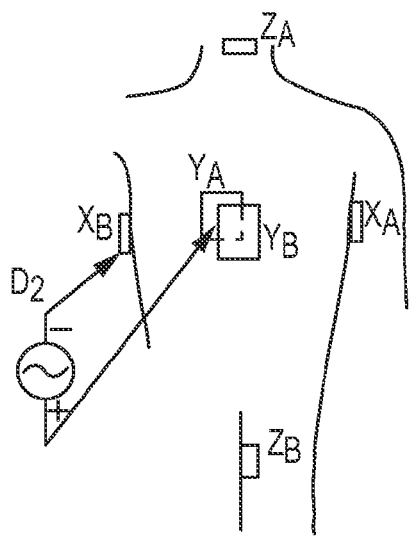
Figure 4D:
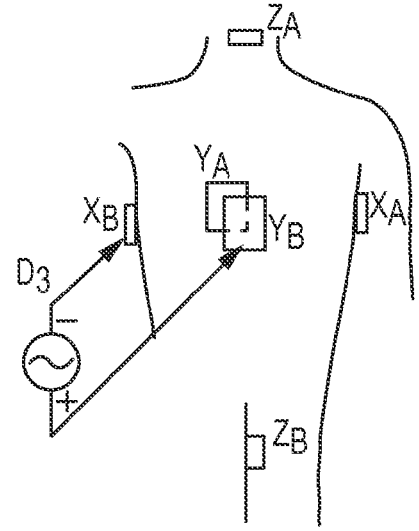

When disposed within the electric fields, the sensor 32 experiences voltages that are dependent on the location between the patch electrodes 38 and the position of the sensor 32 relative to tissue. Voltage measurement comparisons made between the sensor 32 and the patch electrodes 38 can be used to determine the location of the sensor 32 relative to the tissue. Accordingly, as the catheter 12 is swept about or along a particular area or surface of interest, the processing apparatus 16 receives signals (location information) from the sensor 32 reflecting changes in voltage levels on the sensor 32 and from the non-energized patch electrodes 38. Using various known algorithms, the processing apparatus 16 may then determine the location (position and orientation) of the sensor 32 and record it as a location data point 46 (also referred to herein as "data point 46") corresponding to a location of the sensor 32, and therefore, a point on the surface of the desired structure being modeled, in a memory or storage device, such as memory 47, associated with or accessible by the processing apparatus 16. In an exemplary embodiment, prior to recording the location as a location data point, the raw location data represented by the signals received by the processing apparatus 16 may be corrected by the processing apparatus 16 to account for respiration, cardiac activity, and other artifacts using known or hereafter developed techniques. In any event, the collection of location data points 46 ($46_1$, $46_2$, . . . , $46_n$) taken over time results in the formation of a point cloud 48 stored in the memory or storage device. FIG. 3 is illustrative of the point cloud 48 comprising data points $46_1$-$46_{10}$ corresponding to a particular desired structure being modeled.

While the description above has thus far been generally with respect to an orthogonal arrangement of the patch electrodes 38, the present disclosure is not meant to be so limited. Rather, in other exemplary embodiments, non-orthogonal arrangements may be used to perform the position sensing function and to collect the location data points 46. For example, and in general terms, FIGS. 4a-4d depict a plurality of exemplary non-orthogonal dipoles $D_0$, $D_1$, $D_2$, and $D_3$, set in a coordinate system 49. In FIGS. 4a-4d, the X-axis patch electrodes are designated $X_A$ and $X_B$, the Y-axis patch electrodes are designated $Y_A$ and $Y_B$, and the Z-axis patch electrodes are designated $Z_A$ and $Z_B$. For any desired axis, the potentials measured across an intra-cardiac sensor, such as sensor(s) 32, resulting from a predetermined set of drive (source sink) configurations may be combined algebraically to yield the same effective potential as would be obtained simply by driving a uniform current along the orthogonal axes. Any two of the surface electrodes $38_{X1}$, $38_{X2}$, $38_{Y1}$, $38_{Y2}$, $38_{Z1}$, and $38_{Z2}$ (See FIG. 2) may be selected as a dipole source and drain with respect to a ground reference, e.g., the belly patch $38_B$, while the unexcited patch electrodes measure voltage with respect to the ground reference. The sensor(s) 32 placed in the heart 20 is also exposed to the field for a current pulse and is measured with respect to ground, e.g., the belly patch $38_B$.

Data sets from each of the patch electrodes and the sensor(s) 32 are all used to determine the location of the sensor(s) 32 within the heart 20. After the voltage measurements are made, a different pair of patch electrodes is excited by the current source and the voltage measurement process of the remaining patch electrodes and internal sensors takes place.

Whether an orthogonal or non-orthogonal arrangement is used, once a plurality of location data points 46 are collected and recorded, the point cloud 48 of which the plurality of location data points 46 are a part is processed by the processing apparatus 16 to construct a surface model of the structure to which the location data points 46 correspond. The surface model may be a complete surface model of the heart 20, a particular chamber thereof, or a partial surface thereof, for example. Further, the surface model may be either a two-dimensional (2D) or a three-dimensional (3D) surface model. The processing apparatus 16 may employ a number of algorithms or techniques to generate the surface model.

Figure 5:
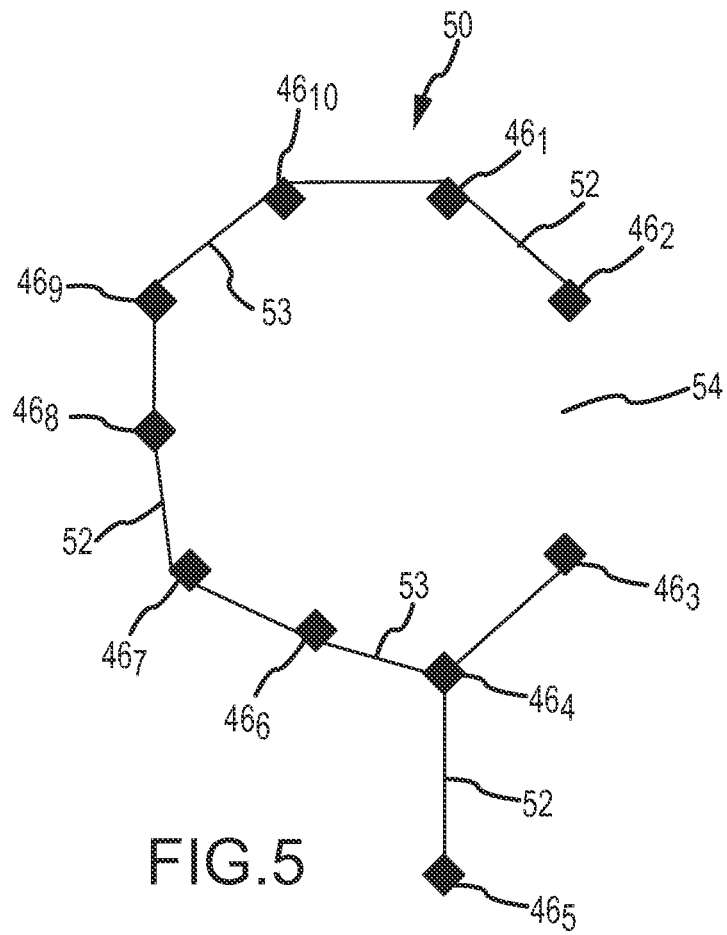
FIG. 5 is a schematic view of a computed two-dimensional alpha shell of the point cloud illustrated in FIG. 3.

For example, in one embodiment, an alpha shape algorithm may be used. In such an embodiment, the location data points 46 of the point cloud 48 are subjected to an alpha shape algorithm to compute an alpha shell 50 corresponding to the desired structure. FIG. 5 is an illustration of a two-dimensional alpha shell 50 of the point cloud 48 depicted in FIG. 3. Any known alpha shape algorithm may be used to compute the alpha shell 50. Regardless of the specific algorithm used, and in the most general sense, the algorithm processes the location data points 46 to form one or more facets 52 that, when taken together, create a surface model of the desired structure. In an instance wherein the alpha shell 50 is two-dimensional, the facets 52 comprise the line segments connecting a pair of data points 46, and therefore, have a single edge 53 (best shown in FIGS. 5 and 8). In an instance wherein the alpha shell 50 is three-dimensional, the facets 52 comprise triangularly-shaped facets generated by the triangulation of the data points 46, and therefore, have three edges 53 (best shown in FIGS. 10*a*-13). Once the alpha shell 50 has been computed, the processing apparatus 16 may generate an electronic signal representative of the alpha shell 50 and transmit the signal to the display device 44 where the alpha shell may be displayed, or to another component or memory/storage device of the model construction system 14 or the system 10.

As those of ordinary skill in the art will appreciate, the more facets 52 in the generated alpha shell or surface model, the more detail of the underlying structure is represented. The number of facets 52, and therefore, the level of detail, depends substantially on the particular value of alpha (a measure of distance on the order of millimeters) that is used in the alpha shape algorithm. For example, if alpha is zero, the alpha shell is simply the original set of points that comprise the point cloud 48. On the other hand, if alpha is infinity, the alpha shell is simply the convex hull of the point cloud 48. Thus, if the value of alpha is relatively small, the model will have a greater degree of detail (i.e., more facets 52) than if the value of alpha is relatively large. In one embodiment provided for exemplary purposes only, the alpha value used is 5.5 mm. It will be appreciated, however, that the present disclosure is not meant to be limited to any one particular alpha value, and that embodiments wherein the alpha value is greater than or less than 5.5 mm remain within the spirit and scope of the present disclosure.

It will be appreciated that while the description above and below is primarily with respect to the use of alpha shape algorithms to generate and/or repair a surface model, the present invention is not meant to be so limited. Rather, in other exemplary embodiments, other surface model generation techniques, such as, for example, and without limitation, a convex hull technique or other like techniques, may be used. Accordingly, the present disclosure is not limited solely to the use of alpha shape algorithms but rather the alpha shape technique is provided for illustrative purposes only.

As described in the Background above, one drawback to conventional surface model generation algorithms and techniques, such as the alpha shape technique or alpha shape algorithms, is that the surface models constructed from point clouds tend to have undesirable defects, such as, for example, missing facets, non-manifold vertices (i.e., a vertex is considered to be non-manifold if it is shared by facets that do not make a single ordered loop around that vertex), and voids or holes that cannot be filled in a way that makes the final surface model manifold (i.e., each edge of the model is shared by no more than two facets). An example of a defect/hole in a surface model is illustrated in FIG. 5, which depicts a two-dimensional surface model or alpha shell 50 of the point cloud 48 illustrated in FIG. 3 that has a hole 54 therein.

In order to correct for defects a surface model (whether generated by the processing apparatus 16 or obtained thereby from another component of the model construction system 14, the system 10, or otherwise), the processing apparatus 16 is configured to perform post-processing operations on the surface model or alpha shell 50 to correct or repair defects in the acquired surface model. The post-processing operations may comprise one or more of a number of techniques or forms, however, common to each technique or form is the adding of additional location data points to the point cloud 48, and then the updating of the surface model or alpha shell 50 by computing an alpha shell of either the added data points alone, or the combination of the original data points 46 and the added data points. The adding of additional data points to the point cloud provides a greater density and distribution of data points to be used in the surface model generation/repair, which thereby results in an alpha shape/surface model with fewer defects.

A number of exemplary techniques for adding additional location data points will be described in turn below. The techniques described below are provided for exemplary purposes only and are not meant to be limiting in nature. It will be appreciated by those having ordinary skill in the art that techniques other than those described below may be used to add additional data points and to update the surface model or alpha shell 50, and such other techniques remain within the spirit and scope of the present disclosure.

Figure 6:
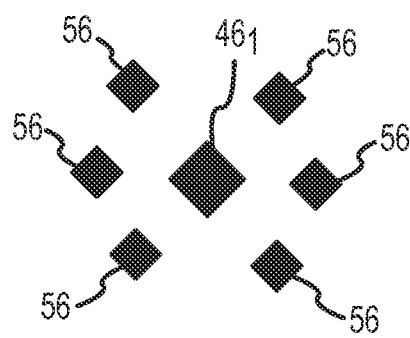
FIG. 6 is a schematic view of a portion of the point cloud illustrated in FIG. 3 containing additional data points added using an exemplary data point adding technique in accordance with the present teachings.
Figure 7:
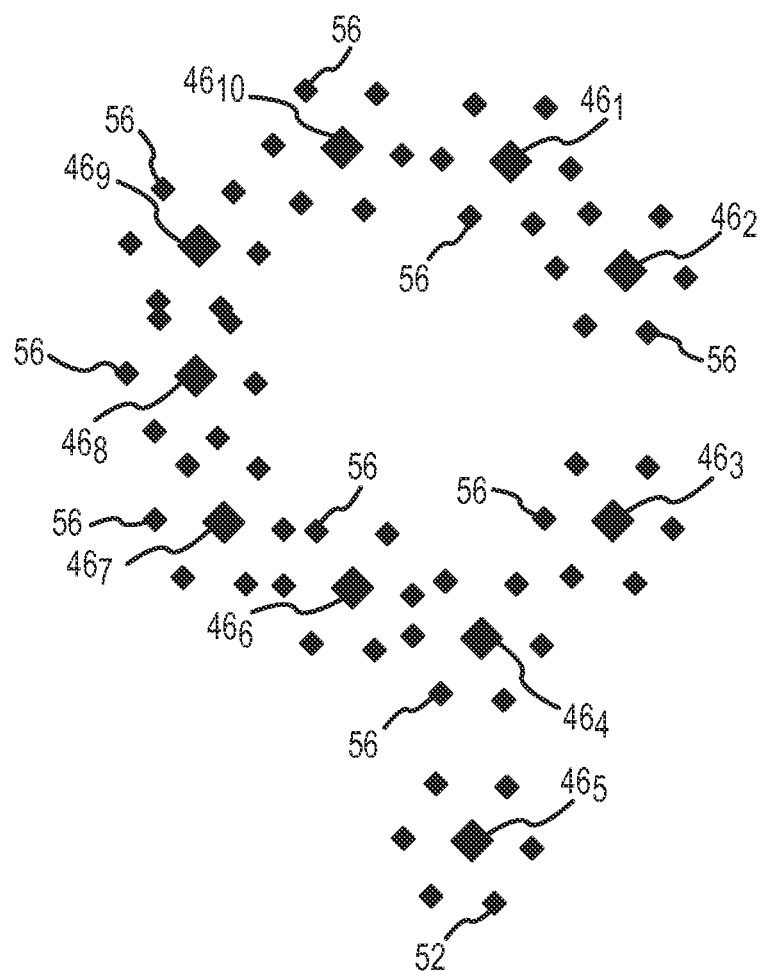
FIG. 7 is a schematic view of the point cloud illustrated in FIG. 3 containing additional data points added using the exemplary data point adding technique illustrated in FIG. 6.

In one exemplary embodiment, the processing apparatus 16 is configured to add additional data points by adding a plurality of new data points 56 around each of the data points 46 of the point cloud 48 (or each vertex of the alpha shell 50). More particularly, and as illustrated in FIGS. 6 and 7, the processing apparatus 16 is configured to use each data point 46 as a center about which new data points 56 are added.

In an exemplary embodiment, the new data points 56 are added by centering on each data point 46 a geometric shape having a plurality of vertices that are uniformly spaced on a sphere of a desired radius, and then adding a new data points at each vertex of the geometric shape. In another exemplary embodiment wherein the alpha shell 50 is two-dimensional, a planar geometric shape may be centered on one or more of the data points 46. In either embodiment, any number of geometric shapes may be used. For example, in one embodiment the processing apparatus 16 is configured to center an icosahedron on each data point 46 and to thus add twelve new data points 56 corresponding to each of the twelve vertices of the icosahedron. In other exemplary embodiments, geometric shapes such as cube, a tetrahedron, and other shapes having a plurality of vertices uniformly spaced on a sphere may be used and remain within the spirit and scope of the present disclosure. In still other embodiments, geometric shapes such as hexagons, pentagons, and any number of other polygonal shapes may be used, and each remains within the spirit and scope of the present disclosure. However, for purposes of clarity and illustration, the description below will be with respect to the use of an icosahedron. In such an embodiment, each of the new data points 56 are spaced from the respective location data point 46 about which the new data points 56 are centered by a distance that is equal to the radius of the icosahedron.

The radius used for adding the new data points 56 may be dependent upon a number of factors. One such factor is the size of the catheter 12 and/or sensor(s) 32 being used to collect the data points 46 (e.g., width, diameter, length, and the like). This is because, in an exemplary embodiment, data points 46 collected by a sensor 32 correspond to the center of the electrical activity of the sensor 32, and therefore, correspond to the center point of the sensor 32—and not the surface of the sensor 32 that is actually contacting the desired structure. Thus, in an exemplary embodiment, the radius used to add new data points 56 around some or all of the data points 46 corresponds to the distance between the center point of the sensor 32 and the outer surface thereof such that new data points 56 are added that more accurately represent the location of the desired structure the sensor 32 was in contact with when the data point 46 was collected, and therefore, more accurately represent the outermost boundary of the desired structure being modeled. These new data points 56, and the outermost points, in particular, may then be used to construct a more realistic or true model or representation of the desired structure.

A limitation on the adding of new data points 56 in accordance with a predetermined radius arises, however, when the sensor 32 is not only in contact with the surface of the desired structure, but is also pressed into the surface of the structure, thereby causing the true outer boundary to be temporarily displaced (i.e., the outer boundary is extended outwardly). As a result, if new data points 56 are added around a data point 46 collected at, and corresponding to, an area wherein the outer boundary of the structure is displaced, the added new data points 56 would lay outside of the true outer boundary of the structure, thereby rendering inaccurate any model or representation based thereon.

Figure 9:
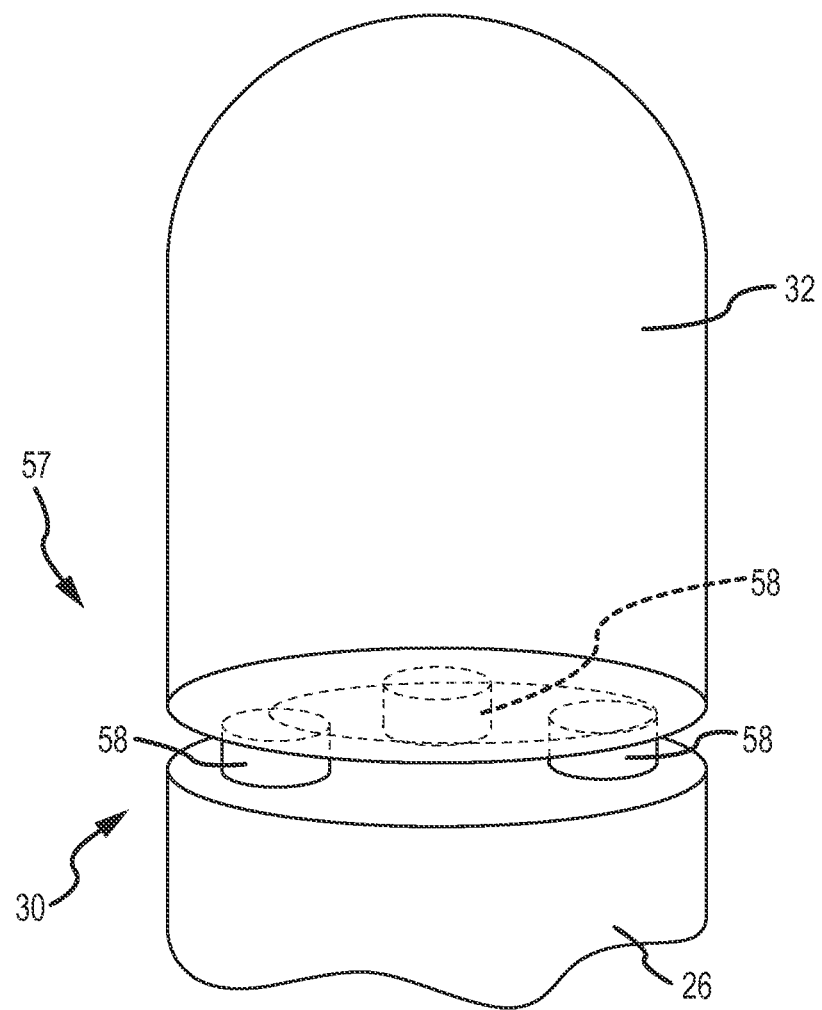
FIG. 9 is a diagrammatic view of a distal portion of a catheter including a force/pressure assembly in accordance with the present teachings.

Accordingly, in an exemplary embodiment, the catheter 12 includes a force or pressure sensor assembly 57 electrically connected to the processing apparatus 16 that is configured to measure the amount of force or pressure applied to the surface of the structure by the catheter 12. The force/pressure sensor assembly 57 may comprise one or more sensors 58 disposed generally at or near the distal end 30 of the catheter shaft 26, and in an exemplary embodiment illustrated in FIG. 9, adjacent a base portion of a sensor 32 disposed at the distal most end of the catheter shaft 26. The sensors 58 are configured to measure the force/pressure applied to the surface of the structure by the catheter 12, and to provide a force or pressure signal indicative of the same. Accordingly, for each collected data point 46, a force/pressure measurement can be acquired. The force/pressure assembly 57 may take the form of any one of a number of force/pressure assemblies, such as, for example and without limitation, that described in U.S. Patent Application Publication No. 2010/0168620 filed on Dec. 31, 2008, the entire disclosure of which is hereby incorporated by reference.

Once the force/pressure is measured by the force/pressure sensor assembly 57, it is compared to a predetermined threshold value. If the measured force exceeds (or, in an exemplary embodiment, meets or exceeds) the predetermined force/pressure threshold value, the processing apparatus 16 may not add any new data points 56 around that data point 46, or may at least limit or reduce the number of new data points 56 added to exclude those that would be disposed beyond the outer boundary of the structure.

The pressure/force threshold value may be set in a number of ways. In one embodiment, the threshold value is set prior to the system 10 being used and is not adjustable. Alternatively, in another exemplary embodiment the threshold value may be adjustable by the user (e.g., different thresholds may correspond to different types of anatomical structures and so the threshold value may be adjusted depending on the type of structure being modeled). In the latter embodiment, the user may be able to set or adjust the threshold value using, for example, a user interface 59 (best shown in FIG. 1). Alternatively, the processing apparatus 16, or another component of the system 10 electrically connected to and configured for communication with the processing apparatus 16, may have a memory or other storage device, such as, for example, a memory 47 illustrated in FIG. 1, that contains a plurality of threshold values. In such an embodiment, the processing apparatus 16 may be configured to present the user with the different threshold value options on the display device 44, for example, and the user may then select the desired threshold value using the user interface 59. Accordingly, the processing apparatus 16 may acquire the threshold value in a number of ways and/or from a number of sources, all of which are within the spirit and scope of the present disclosure.

In any event, in an embodiment wherein the catheter 12 has a force/pressure sensor assembly 57, the processing apparatus 16 is configured to take into account the amount of force being applied to the surface of the structure in adding new data points 56 around a particular data point 46.

Accordingly, in an exemplary embodiment, the size of the catheter 12 and/or the sensor 32 dictates the magnitude of the radius used to add new data points 56. In one exemplary embodiment provided for illustrative purposes only, the catheter 12 is a six French (6 F) electrophysiological catheter. In such an embodiment, a radius of 1 mm is used because the data points are collected at the center of the sensor 32 and 1 mm ensures that the new data points 56 being added will be within the cardiac chamber and give a better approximation of the true surface location. Accordingly, when the processing apparatus 16 centers the icosahedron on a data point 46, the new data points 56 corresponding to the vertices of the icosahedron will each be disposed 1 mm from the data point 46. It will be appreciated, however, that the radius value may be more or less than 1 mm depending on, for example, the particular catheter and/or the size or dimensions of the sensor(s) 32 used in the data point collection, and therefore, embodiments wherein the radius is greater or less than 1 mm remain within the spirit and scope of the present disclosure.

In one embodiment, the radius is set prior to the system 10 being used and is not adjustable. Alternatively, in another exemplary embodiment the radius value may be adjustable by the user. In the latter embodiment, the system 10 may include a user interface 59 (best shown in FIG. 1), such as, for example, a touch screen, a keyboard, a keypad, a slider control, a graphical user interface having one or more user-selectable or user-inputtable fields, or some other user-controllable input device electrically connected to the processing apparatus 16 to allow the user to set up or adjust the radius value. Alternatively, the processing apparatus 16, or another component of the system 10 electrically connected to and configured for communication with the processing apparatus 16, may have a memory or other storage device (e.g., memory 47 illustrated in FIG. 1) that contains a plurality of radius values. In such an embodiment, the processing apparatus 16 may be configured to present the user with the different radius value options on the display device 44, for example, and the user may then select the desired radius value using the user interface 59. In yet another exemplary embodiment, the catheter 12 may itself include a memory such as an EEPROM that stores one or more predetermined radius values corresponding to that particular catheter, or stores a memory address for accessing the radius value(s) in another memory location. The processing apparatus 16 may acquire the radius value(s) by retrieving the information from the appropriate memory location. Accordingly, the processing apparatus 16 may acquire the radius value to be used in a number of ways and/or from a number of sources, all of which are within the spirit and scope of the present disclosure.

In another exemplary embodiment, rather than adding new data points 56 around each of the data points 46 of the point cloud 48, the processing apparatus is configured to add new data points 56 around less than all of the data points 46. Therefore, embodiments wherein less than all of the data points 46 are used in adding new data points 56 remain within the spirit and scope of the present disclosure.

Figure 8:
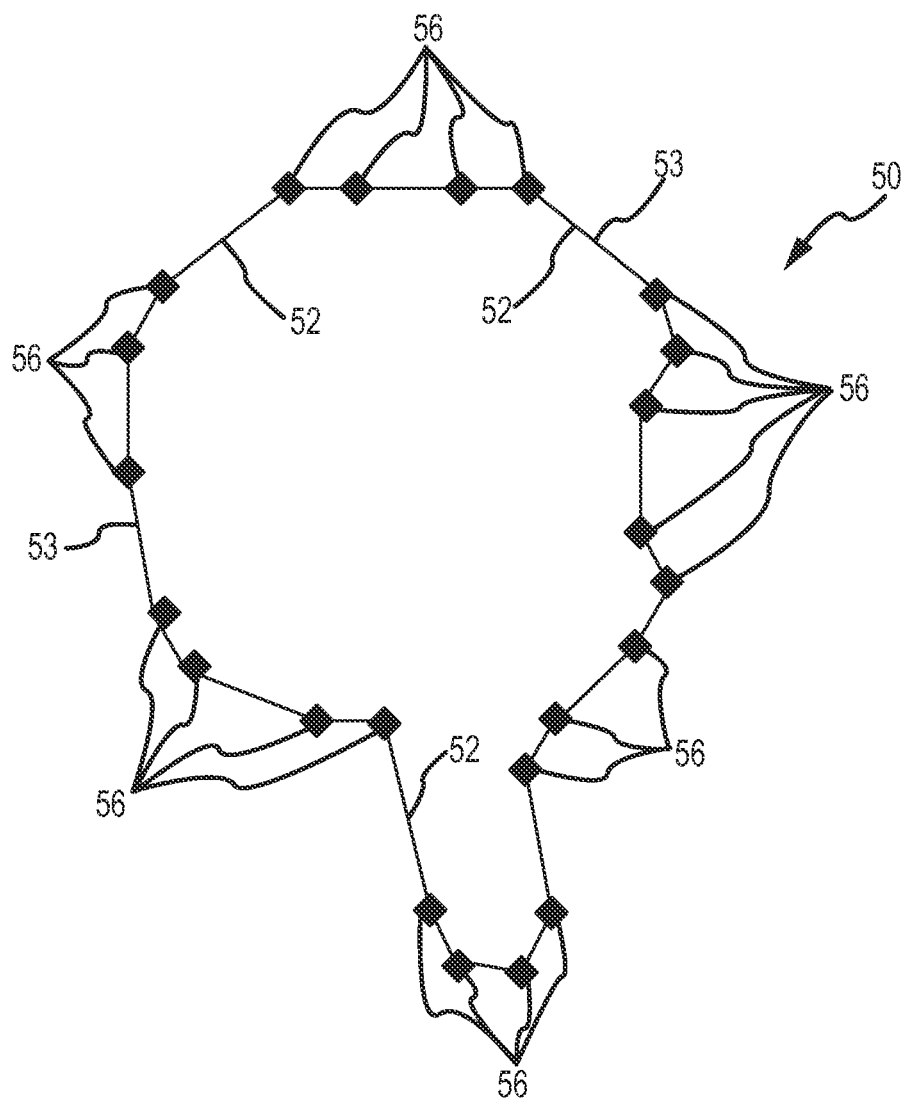
FIG. 8 is a schematic view of a computed two-dimensional alpha shell of the point cloud illustrated in FIG. 7.

As will be described below, once the processing apparatus 16 has added all of the new data points 56 that are necessary (e.g., the processing apparatus has processed all the data points 46, or a subset thereof, and has added new points 56 around each of the appropriate data points 46), the processing apparatus is configured to compute an alpha shell of either the new data points 56 alone, or the combination of the data points 46 and the new data points 56, to update the alpha shell 50, and therefore, the surface model of the anatomic structure (See FIG. 8, which depicts a two-dimensional alpha shell of the point cloud illustrated in FIG. 7).

In another exemplary embodiment, the processing apparatus 16 is configured to add additional data points by first evaluating each facet 52 of the alpha shell 50 and then, if necessary, refining the edges 53 thereof prior to adding additional data points. More particularly, in one embodiment, the processing apparatus 16 is configured to evaluate the lengths of each edge 53 of each facet 52 to determine whether any of the edges 53 have a length that exceeds a predetermined threshold value. In an embodiment wherein the alpha shell 50 is two-dimensional, each facet 52 comprises a single edge 53, and so the edges 53 of the alpha shell 50 are evaluated. Alternatively, in an embodiment wherein the alpha shell 50 is three-dimensional, each facet 52 has a triangular shape and therefore comprises three edges 53. In such an embodiment, each edge 53 of each facet 52 is evaluated.

In either instance, if no edges 53 are found to exceed the threshold value, then no edge refinement is required. If, however, one or more edges 53 are found to exceed the threshold value, those edges 53 are refined using, for example, those techniques described in greater detail below. Once this process is complete for a given facet 52, it may be repeated for each of the other facets 52 of the alpha shell 50 to be evaluated in accordance with a predetermined sequence. It will be appreciated that while in one embodiment each facet 52 and/or each edge 53 of each facet 52 is evaluated, in other exemplary embodiments, less than all of the facets 52 and/or edges 53 thereof are evaluated. For example, in one embodiment, only those edges 53 that are boundary edges (e.g., free edges or edges that are not shared by more than one facet 52) of the alpha shell 50, or those facets 52 containing a boundary edge of the alpha shell 50, are evaluated in the manner described above. Accordingly, embodiments wherein every facet 52 and/or every edge 53 of every facet 52 are evaluated, and embodiments wherein less than every facet 52 and/or less than every edge 53 of every facet 52 are evaluated both remain within the spirit and scope of the present disclosure.

The threshold value used to evaluate edge length may be set in a number of ways. In one embodiment, the threshold value is set prior to the system 10 being used and is not adjustable. Alternatively, in another exemplary embodiment the threshold value may be adjustable by the user. In the latter embodiment, the user may be able to set or adjust the threshold value using, for example, the user interface 59 (best shown in FIG. 1). Alternatively, the processing apparatus 16, or another component of the system 10 electrically connected to and configured for communication with the processing apparatus 16, may have a memory or other storage device, such as, for example, the memory 47 illustrated in FIG. 1, that contains a plurality of threshold values. In such an embodiment, the processing apparatus 16 may be configured to present the user with the different threshold value options on the display device 44, for example, and the user may then select the desired threshold value using the user interface 59. Accordingly, the processing apparatus 16 may acquire the threshold value in a number of ways and/or from a number of sources, all of which are within the spirit and scope of the present disclosure. In one embodiment provided for exemplary purposes only, the threshold value is 3 mm. It will be appreciated, however, that the present disclosure is not meant to be limited to any particular threshold value, but rather embodiments wherein the threshold value is greater than or less than 3 mm remain within the spirit and scope of the present disclosure.

Figure 10C:
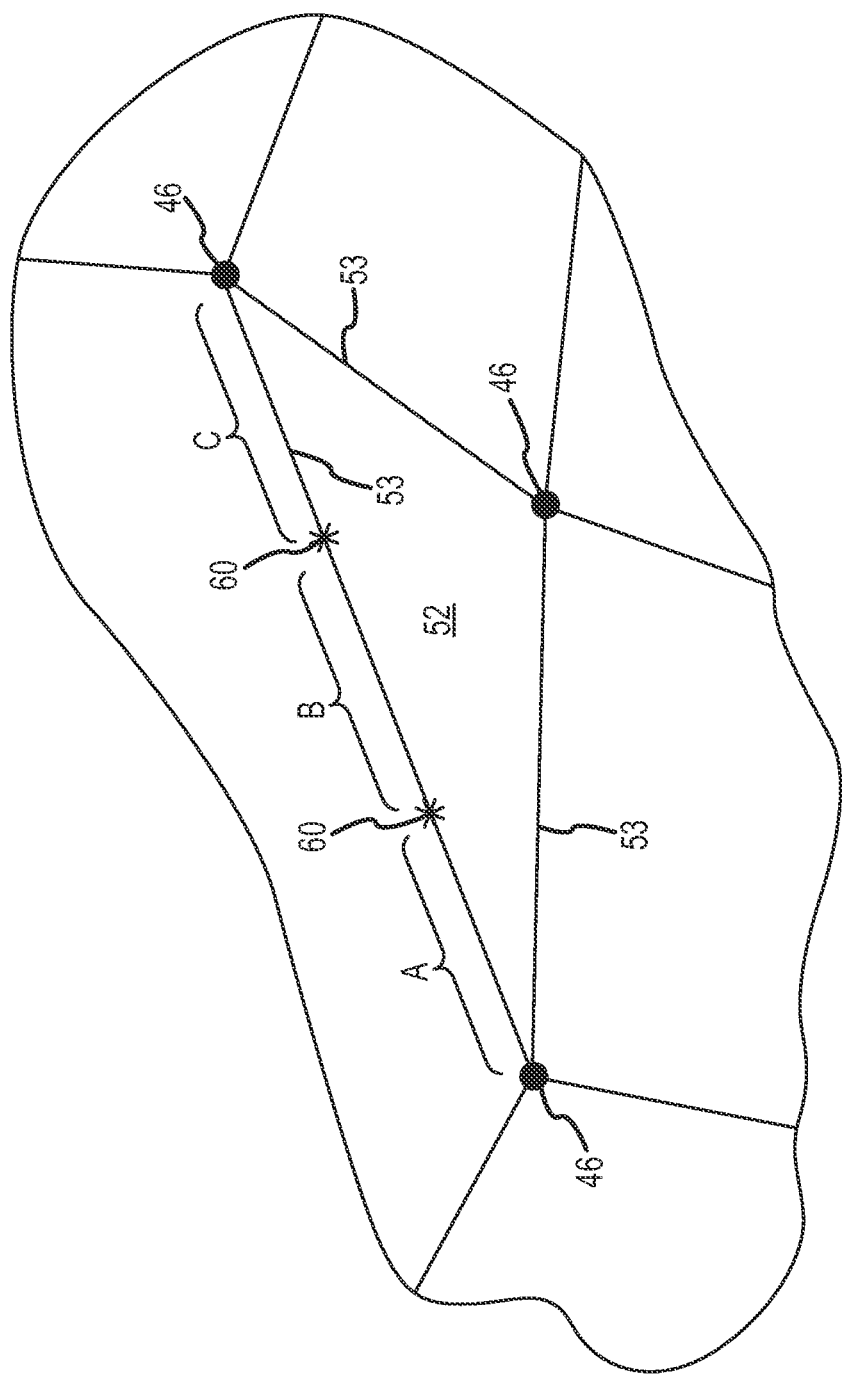

As briefly described above, if any evaluated edges 53 are deemed to exceed the threshold value, those edges 53 are refined. One technique that may be used to refine such edges 53 is a segmentation technique. More particularly, each edge 53 having a length that exceeds the threshold value is divided in to a plurality of segments wherein each segment has a length that either equals or is less than the threshold value. For example, and with reference to FIG. 10*a*, which depicts an enlarged portion of a three-dimensional alpha shell 50 having triangularly-shaped facets 52, if an edge 53 has a length that is twice the threshold value, the edge 53 may be divided into two (or more) segments—"A" and "B"—each having a length equal to or less than the threshold value. Similarly, and with reference to FIG. 10*b*, if an edge 53 is one-and-a-half times the length of the threshold value, the edge 53 may be divided into two (or more) segments—"A" and "B"—with one segment having a length equal to the threshold value and the other segment having a length equal to half of the threshold value. Alternatively, the edge 53 may be divided into segments having equal lengths (e.g., each segment having a length 0.75 times the threshold value), or unequal lengths, each of which either meets or is below the threshold value. With reference to FIG. 10*c*, if an edge 53 has a length that is three times the threshold value, the edge 53 may be divided into three (or more) segments—"A", "B", and "C"—each having a length equal to the threshold value. Alternatively, the edge 53 may be divided into segments having unequal lengths, each of which either meets or is below the threshold value.

As a result of the segmentation, one or more refined data points 60 are added to the point cloud 48. For example, and with reference to FIGS. 10*a* and 10*b*, if an edge 53 of a facet 52 is divided into two segments, one refined data point 60 is added to the evaluated edge 53. With reference to FIG. 10*c*, if an edge 53 is divided into three segments, two refined data points 60 are added to the evaluated edge 53. Accordingly, the number of refined data points 60 added to an edge is one less than the number of segments into which the edge is divided.

Once each edge 53 of each facet 52, or at least one or more edges 53 of certain predetermined facets 52, in the alpha shell 50 have been evaluated and, if applicable, refined, the processing apparatus 16 may be further configured to add new data points 56 to the point cloud 48. In an exemplary embodiment, only the refined data points 60 are used to add the new data points 56. However, in another exemplary embodiment, both refined data points 60 and data points 46 are used. In either embodiment, the processing apparatus 16 is configured to add a plurality of new data points 56 around data points 46 and/or refined data points 60. More particularly, and as described in greater detail above, in an exemplary embodiment the processing apparatus 16 is configured to use data points 46 and/or refined data points 60 as centers about which new data points 56 are added. This may be accomplished using the same technique described in great detail above wherein a geometric shape is centered on the data points 46 and new data points 56 are added at each vertex of the geometric shape. Accordingly, the description of this technique set forth above is incorporated here by reference and will not be repeated. It will be appreciated that while in one embodiment every data point 46 and/or every refined data point 60 is used to add new data points 56 to the point cloud 48, in other exemplary embodiments, less than all of the data points 46 and/or refined data points 60 are used. Accordingly, embodiments wherein a subset of the data points 46 and/or refined data points 60 are used to add new data points 56 remain within the spirit and scope of the present disclosure.

As will be described below, once the processing apparatus 16 has added all of the additional data points (e.g., new data points 56 and refined data points 60) that are necessary or desired (e.g., the processing apparatus has processed all of the desired edges 53 of the facets 52 of the alpha shell 50 and has refined the edges 53 as necessary), and has added new points 56 around each of the appropriate data points 46 and/or refined data points 60, the processing apparatus 16 is configured to compute an alpha shell of either the new data points 56 alone or the combination of some or all of the data points 46, the refined data points 60, and the new data points 56 to update the alpha shell 50, and therefore, the surface model of the anatomic structure.

In another exemplary, rather than refining edges 53 of the alpha shell 50 by segmenting those edges 53 having lengths that exceed a predetermined threshold value, the processing apparatus 16 is configured to refine such edges 53 by dividing the facets 52 of which the edges 53 are a part into a plurality of new triangularly-shaped facets, and then evaluating the edges 53 of the resulting plurality of new facets 52 in the same manner as described above. More particularly, and with reference to FIGS. 11a-11c, in one embodiment, the processing apparatus 16 evaluates each facet 52 of the alpha shell 50 individually to determine whether any of the three edges 53 thereof exceed the predetermined threshold value. The value of the threshold is determined in the same manner described above with respect to the segmentation refinement technique, and therefore, is incorporated here by reference and will not be repeated.

For purposes of clarity of explanation, the facet 52 illustrated in FIG. 11a, which depicts an enlarged portion of a three-dimensional alpha shell 50 having triangularly-shaped facets 52, will be the facet being evaluated by the processing apparatus 16. If it is determined that no edges 53 of the facet 52 have a length that exceeds the predetermined threshold value, the aforedescribed process is repeated for the next facet 52 of the alpha shell 50 that is to be evaluated in accordance with a predetermined sequence. If, however, it is determined that at least one edge 53 of the facet 52 has a length that exceeds the threshold value, one or more refined data points 60 are added to each edge 53 of the facet 52.

Figure 11B:
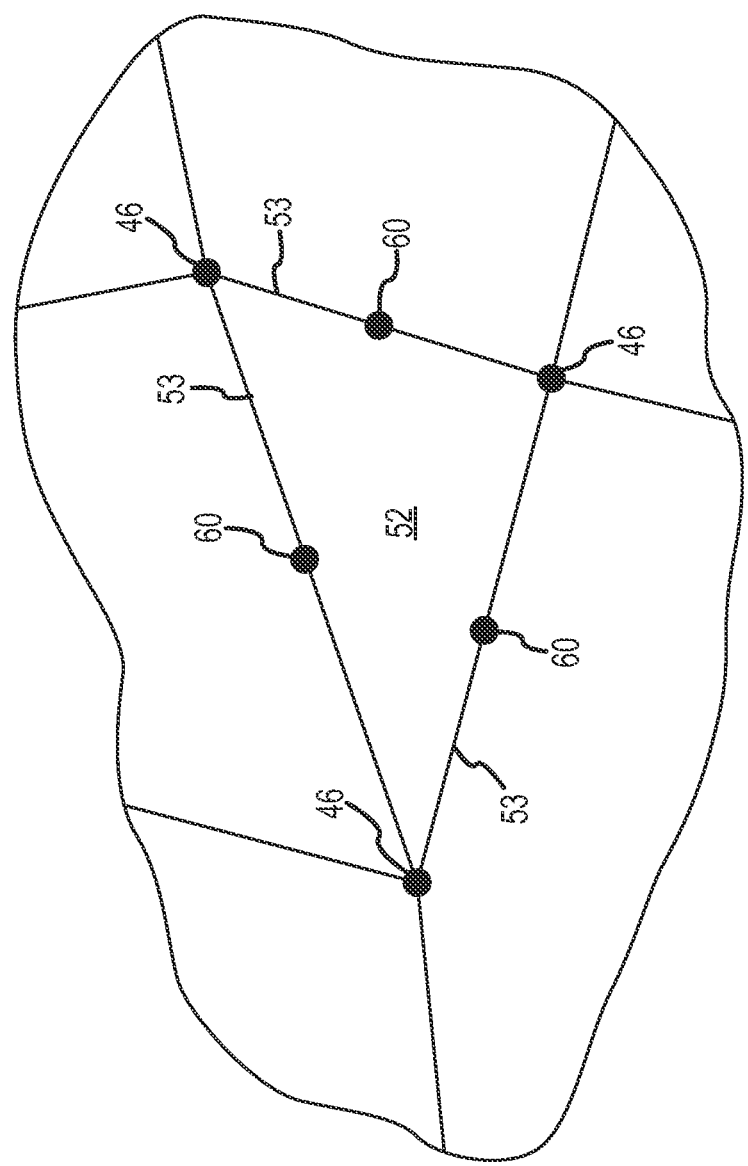
Figure 12:
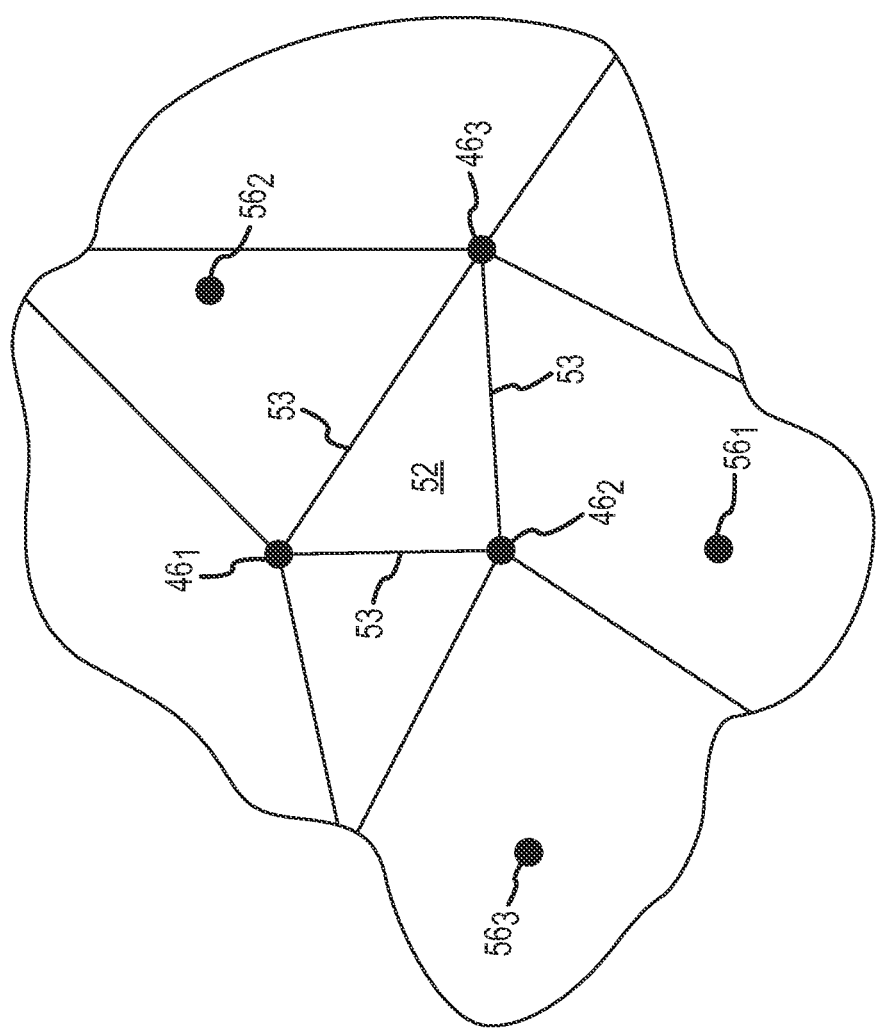
FIG. 12 is an enlarged view of a portion of a three-dimensional alpha shell depicting triangularly-shaped facets thereof and illustrating yet still another exemplary data point adding technique wherein each vertex of a facet is reflected across the edge of the facet opposite the reflected vertex, and new data points are added at the corresponding locations.

In the embodiment illustrated in FIGS. 11a-11c, one refined data point 60 is added at the midpoint of each edge 53 of the facet 52 (See FIG. 11b). The refined data points 60 are then triangulated to break the facet 52 into a plurality of new facets. In the illustrated embodiment, four new facets—facets $52_1, 52_2, 52_3, 52_4$ (See FIG. 11c) are created. In an exemplary embodiment, the process described above is then repeated for each of the "new" facets—e.g., facets $52_1$-$52_4$—in the same manner described above to determine if any edge 53 of any of the facets $52_1$-$52_4$ exceeds the predetermined threshold value. If not, the process moves to the next facet 52 in the alpha shell 50 that is to be evaluated in accordance with a predetermined sequence. If, however, one or more of the edges 53 has a length that exceeds the threshold value, the process described above repeats itself for the facets(s) $52_1$-$52_4$ to which those edges 53 correspond.

In an exemplary embodiment, this process is performed and/or repeated for each facet 52 in the alpha shell 50 until all of the edges 53 of the alpha shell 50 have a length that is within the threshold value. In other exemplary embodiments, however, less than all of the facets 52 are evaluated in the manner described above. For example, in one embodiment, only the facets 52 that contain a boundary edge of the alpha shell 50 are evaluated. Accordingly, embodiments wherein less than all of the facets 52 of the alpha shell 50 are evaluated remain within the spirit and scope of the present disclosure.

Once it is determined that all of the relevant edges 53 in the surface model or alpha shell 50 have lengths that are within the threshold value, the processing apparatus 16 may be configured to add new data points 56 to the point cloud 48. In exemplary embodiment, only refined data points 60 are used to add the new data points 56. However, in another exemplary embodiment, both refined data points 60 and data points 46 are used. In either embodiment, the processing apparatus 16 is configured to add a plurality of new data points 56 around data points 46 and/or refined data points 60. More particularly, and as described in greater detail above, in an exemplary embodiment the processing apparatus 16 is configured to use data points 46 and/or refined data points 60 as centers about which new data points 56 are added. This may be accomplished using the same technique described in great detail above wherein a geometric shape is centered around the data points 46 and new data points 56 are added at each vertex of the geometric shape. Accordingly, the description of this technique set forth above is incorporated here by reference and will not be repeated. It will be appreciated that while in one embodiment every data point 46 and/or refined data point 60 is used to add new data points 56 to the point cloud 48, in other exemplary embodiments, less than all of the data points 46 and/or refined data points 60 are used. Accordingly, embodiments wherein a subset of the data points 46 and/or refined data points 60 are used to add new data points 56 remain within the spirit and scope of the present disclosure.

As will be described below, once the processing apparatus 16 has added all of the new data points 56 that are necessary or desired (e.g., the processing apparatus 16 has processed all of the relevant edges 53 of the facets 52 of the alpha shell 50 and has refined the edges 53 as necessary), and has added new points 56 around each of the appropriate data points 46 and/or refined data points 60, the processing apparatus 16 is configured to compute an alpha shell of either the new data points 56 or the combination of some or all of the data points 46, the refined data points 60, and the new data points 56 to update the alpha shell 50, and therefore, the surface model of the anatomic structure.

In another exemplary embodiment, rather than, or in addition to, adding new data points 56 by centering a geometric shape around one or more data points 46 and/or refined data points 60, new data points 56 may be added beyond each edge 53 of one or more of the facets 52 and within the same plane as the facets 52.

In one embodiment, the processing apparatus 16 is configured to accomplish this by reflecting each vertex or data point 46 of a facet 52 across the edge 53 of the facet 52 that is opposite the reflected data point 46. For example, and with reference to FIG. 12, which depicts an enlarged portion of a three-dimensional alpha shell 50 having triangularly-shaped facets 52, the processing apparatus 16 is configured to reflect one or more of the vertices or data points $46_1, 46_2, 46_3$ of the facet 52 to create up to three new data points 56 that are disposed within the same plane as the facet 52. Accordingly, in the illustrated embodiment, the processing apparatus 16 is configured to create new data points $56_1, 56_2, 56_3$ that correspond to data points $46_1, 46_2, 46_3$, respectively.

Once this is completed for one facet 52, the process may be repeated for some or all of the remaining facets 52 in the alpha shell 50, in accordance with a predetermined sequence. For example, in one exemplary embodiment, the aforedescribed process is performed for each facet 52 of the alpha shell 50. However, in other exemplary embodiments, the process is performed for less than all of the facets 52. For instance, in one exemplary embodiment, only the data points 46 that are opposite boundary edges (e.g., free edges or edges that are not shared by more than one facet 52) of the alpha shell 50 are reflected across the boundary edge. Thus, in such an embodiment the process is only performed on those facets 52 containing one or more boundary edges. Accordingly, embodiments wherein the processing apparatus 16 performs the aforedescribed process on less than all of the facets 52, and/or the edges 53 or vertices/data points 46 of a facet 52, of the alpha shell 50 remain within the spirit and scope of the present disclosure.

In another exemplary embodiment, the processing apparatus 16 is configured to add new data points 56 by extending or projecting one or more points on one or more edges 53 of a facet 52 (whether the facet 52 comprises a single edge 53, in the instance wherein the alpha shell 50 is two-dimensional, or three edges 53, in the instance wherein the alpha shell is three-dimensional) a predetermined distance outward from the corresponding edge 53 in the same plane as the facet 52. In one embodiment provided for exemplary purposes only, a single point is projected and the point is the midpoint of the edge 53.

Figure 13:
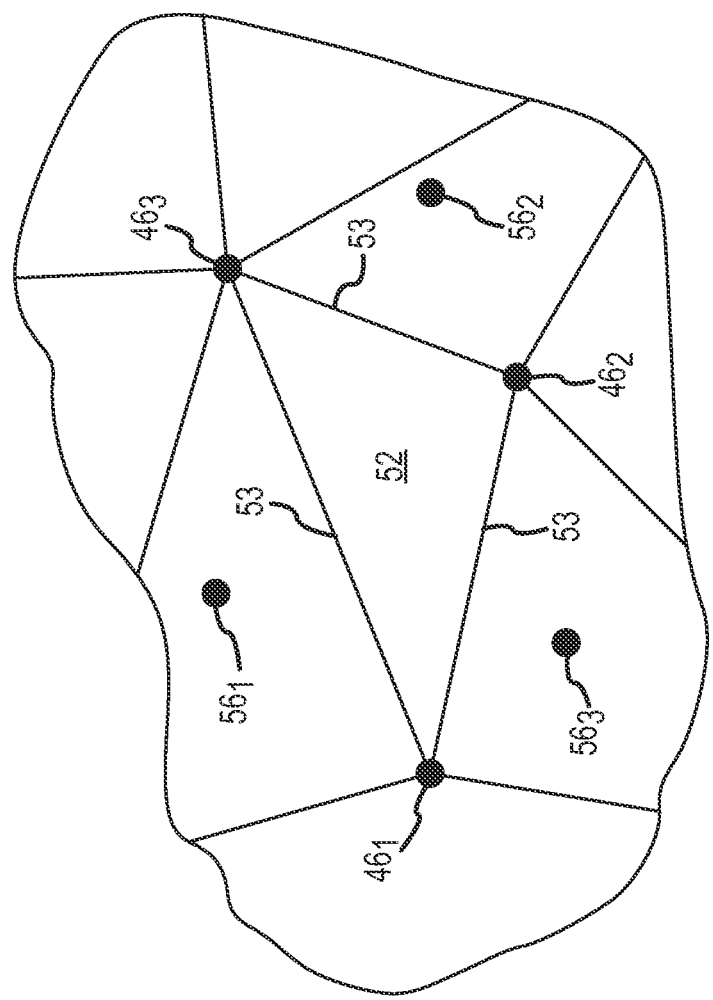
FIG. 13 is an enlarged view of a portion of a three-dimensional alpha shell depicting triangularly-shaped facets thereof and illustrating yet still another exemplary data point adding technique wherein a point on each edge of a facet is projected a predetermined distance outward, and new data points added at the corresponding locations.

For example, in the embodiment illustrated in FIG. 13, which depicts an enlarged portion of a three-dimensional alpha shell 50 having triangularly-shaped facets 52, the processing apparatus 16 is configured to extend the midpoint of each edge 53 of the facet 52 a predetermined distance outward and to then place a new data point 56 at the corresponding location. In an exemplary embodiment, the distance from the edge(s) 53 of the facet 52 at which the new data point(s) 56 are placed is between 1-4 mm. It will be appreciated, however, that the present disclosure is not meant to be limited to any particular distance value, but rather embodiments wherein the distance is greater than or less than 1-4 mm remain within the spirit and scope of the present disclosure. Accordingly, in the illustrated embodiment, the processing apparatus 16 is configured to create new data points $56_1$, $56_2$, $56_3$ that correspond to the midpoints of the respective edges 53 of the facet 52. It will be appreciated that while in the embodiment described above the midpoint of each edge 53 is used to add new data points 56, the present disclosure is not meant to be limited to such an embodiment, rather in other exemplary embodiments the processing apparatus 16 may use one or more points along each edge 53 other than, or in addition to, the midpoint, and such embodiments remain within the spirit and scope of the present disclosure.

Once this is completed for one facet 52, the process may be repeated for some or all of the remaining facets 52 in the alpha shell 50, in accordance with a predetermined sequence. For instance, in one exemplary embodiment, the aforedescribed process is performed for each facet 52 of the alpha shell 50. However, in other exemplary embodiments, the process is performed for less than all of the facets 52. For example, in one embodiment, only those facets 52 containing a boundary edge (e.g., free edges or edges that are not shared by more than one facet 52) of the alpha shell 50 are subjected to the aforedescribed process. Further, in an embodiment wherein the process is only applied to facets 52 containing a boundary edge, points may only be extended or projected from the boundary edge. Accordingly, embodiments wherein the processing apparatus 16 performs the aforedescribed process on less than all of the facets 52 and/or less than all of the edges 53 of a facet 52 remain within the spirit and scope of the present disclosure.

In either of the embodiments described above wherein new data points 56 are added and are disposed within the plane of the corresponding facet 52, the new data points 56 may constitute the additional data points used for updating the alpha shell 50. Alternatively, the new data points 56 may be used to add additional new data points 56 in the manner described above with respect to the data points 46 and the refined data points 60. More particularly, some or all of the new data points 56 created using the techniques of the two embodiments described immediately above may be used as centers about which additional new data points 56 are added. This may be accomplished using the same technique described in great detail above wherein a geometric shape is centered around the data points 46 and new data points 56 are added at each vertex of the geometric shape. Accordingly, the description of this technique set forth above is incorporated here by reference and will not be repeated. It will be appreciated that while in one embodiment every data point 46 and/or every new data point 56 is used to add additional new data points 56 to the point cloud 48, in other exemplary embodiments, less than all of the data points 46 and/or new data points 56 are used. Accordingly, embodiments wherein a subset of the data points 46 and/or new data points 56 are used to add additional new data points 56 remain within the spirit and scope of the present disclosure.

In another exemplary embodiment, the known configuration of the catheter 12 may be taken advantage of to add additional data points to the point cloud 48. More particularly, in an embodiment wherein a plurality of sensors 32 are used to collect data points 46, the spacing or locations of the sensors 32 on the shaft 26 of the catheter 12 relative to each other are known or may be acquired by the processing apparatus 16. Accordingly, when data points 46 are collected by and for each of the plurality of sensors 32 at the substantially same point in time, the processing apparatus 16 may be configured to add new data points 56 in the space(s) between the plurality of sensors 32.

Figure 14A:
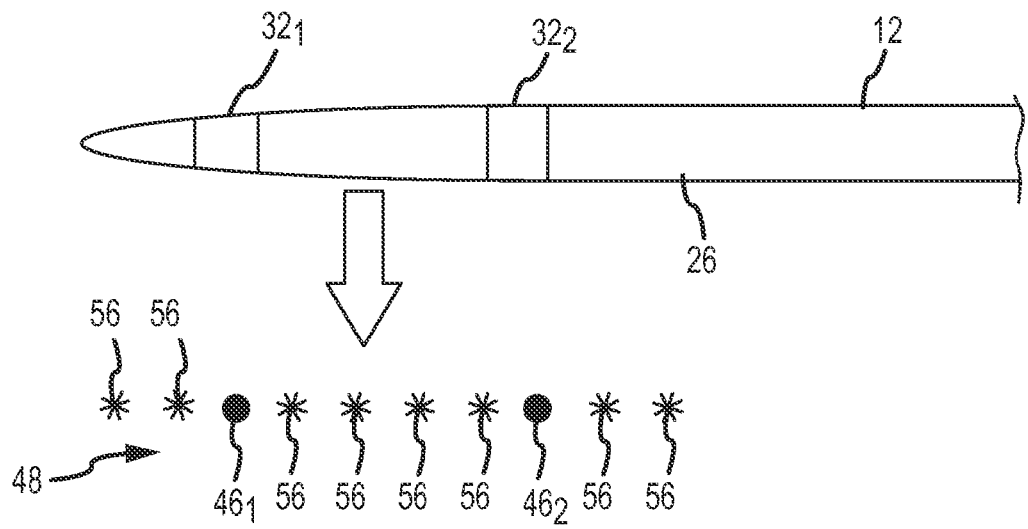
FIGS. 14a and 14b are schematic and diagrammatic views of an exemplary catheter used for collecting data points and illustrating another exemplary data point adding technique wherein new data points are added between, beyond, and/or above and below two data points collected by two different sensors on the catheter.

For instance, and with reference to FIG. 14*a*, in one exemplary embodiment the catheter 12 has a pair of sensors 32 ($32_1$, $32_2$) mounted thereon that are used to collect location data points 46. In such an embodiment, the sensors 32 each collect a respective data point 46 ($46_1$, $46_2$) at a particular point in time. The processing apparatus 16 is configured to recognize that the data points $46_1$, $46_2$ were collected at the same time, and because the processing apparatus 16 knows the spacing and locations of the sensors $32_1$, $32_2$ on the catheter 12 relative to each other, the processing apparatus 16 is configured to add one or more new data points 56 in the space between sensors $32_1$, $32_2$.

In addition to adding one or more data points 56 between the sensors $32_1$, $32_2$, using the known configuration of the catheter 12, the processing apparatus 16 may be further configured to extrapolate one or more new data points 56 beyond the data points 46. Accordingly, and as illustrated in FIG. 14*a*, in addition to or instead of adding data points 56 to the space between sensors $32_1$, $32_2$, the processing apparatus 16 may be configured to add data points 56 beyond the data points 46 (e.g., forward of the distal most sensor $32_1$ and rearward of the proximal-most sensor $32_2$).

Figure 14B:
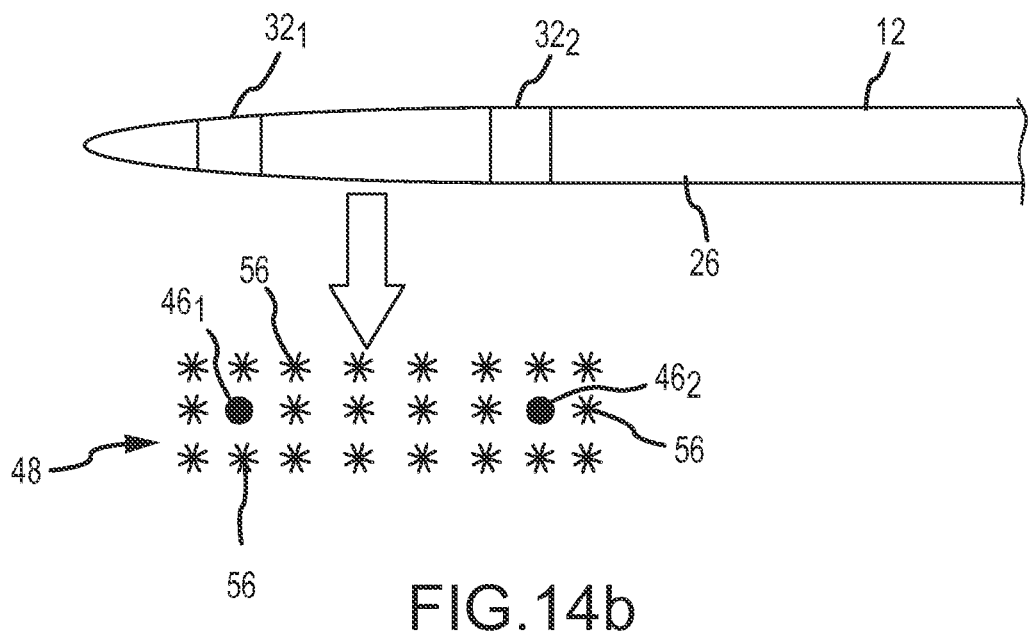

Further, in an exemplary embodiment, because the configuration of the catheter 12 is known, the thickness of the catheter 12 is also known. Accordingly, and as illustrated in FIG. 14*b*, the processing apparatus 16 may be configured to use the known configuration of the catheter 12 to add data points 56 to represent the thickness of the catheter 12 (e.g., adding data points "above" and "below" the data points 46 and/or other added data points 56).

In any event, the number of new data points 56 added may be dependent upon a number of factors, such as, for example and without limitation, the size of the space between the sensors $32_1$, $32_2$, the desired spacing between the data points 46 and the new data points 56, the thickness of the catheter 12 and the sensors 32 thereof, and the desired spacing between each of the new data points 56. Accordingly, the processing apparatus 16 is configured to add an appropriate number of new data points 56 in accordance with, for example, a desired or predetermined scheme.

While the examples provided above are with respect to a catheter having a shaft with a relatively or substantially straight distal portion, it will be appreciated by those having ordinary skill in the art that this technique may be applied in connection with catheters other than those having shafts with straight distal portions, such as, for example, spiral catheters, and thus catheters having other than straight distal portions remain within the spirit and scope of the present disclosure.

The processing apparatus 16 may be configured to acquire the configuration of the catheter 12, and the sensors 32 mounted thereon, in particular, in a number of ways. For example, in one embodiment, the processing apparatus 16 may be configured for use with one particular type/size of catheter, and therefore, may be pre-programmed with the configuration for that particular type/size of catheter. Alternatively, the configuration may have been previously provided by the user and stored in a memory device or storage medium. Thus, the configuration of the catheter may be stored in a memory device or storage medium that is part of or accessible by the processing apparatus 16 (e.g., the memory 47 illustrated in FIG. 1).

In another embodiment, the processing apparatus 16 may be configured for use with one or more types or sizes of catheters, and may be pre-programmed with the configurations for the different types or sizes of catheters with which the processing apparatus 16 is configured to be used. Thus, the configurations of those catheters may be stored in a table in a memory device or storage medium that is part of or accessible by the processing apparatus 16 (e.g., the memory 47 illustrated in FIG. 1). When the system 10 is being used, the processing apparatus 16 may be configured to recognize the type or size of catheter being used, and may be further configured to automatically select the appropriate catheter configuration from a plurality of configurations to use in the adding of the new data points 56. Alternatively, the processing apparatus 16 may be configured to prompt the user to identify the catheter being used at the start-up or initialization of the system 10 and/or the model construction system 14, for example. In such an embodiment, the processing apparatus 16 is configured to receive the information from the user via, for example, the user input device 58 and to then retrieve the appropriate configuration from the memory device or storage medium.

In another exemplary embodiment, rather than accessing a catheter configuration from a memory device or storage medium, the processing apparatus 16 is configured to acquire the configuration by prompting the user to provide the information at the start-up or initialization of the system 10 and/or the model construction system 14, for example. In such an embodiment, the processing apparatus 16 is configured to receive the information from the user via, for example, the user input device 58.

In yet another exemplary embodiment, the catheter itself may include a memory, such as an EEPROM, that stores a configuration corresponding to that particular catheter, or stores a memory address for accessing the configuration in another memory location. The processing apparatus 16 may acquire the configuration by retrieving the information from the appropriate memory location. Accordingly, the processing apparatus 16 may acquire the catheter configuration in a number of ways and/or from a number of sources, all of which are within the spirit and scope of the present disclosure.

In an exemplary embodiment, the new data points 56 may constitute the additional data points used for updating the alpha shell 50. Alternatively, the new data points 56 may be used to add additional new data points 56 in the manner described above with respect to the data points 46 and the refined data points 60. More particularly, some or all of the new data points 56 created using the technique described immediately above may be used as centers about which additional new data points 56 are added. This may be accomplished using the same technique described in great detail above wherein a geometric shape is centered around the data points 46 and new data points 56 are added at each vertex of the geometric shape. Accordingly, the description of this technique set forth above is incorporated here by reference and will not be repeated. It will be appreciated that while in one embodiment every data point 46 and/or every new data point 56 is used to add additional new data points 56 to the point cloud 48, in other exemplary embodiments, less than all of the data points 46 and/or new data points 56 are used. Accordingly, embodiments wherein a subset of the data points 46 and/or new data points 56 are used to add additional new data points 56 remain within the spirit and scope of the present disclosure.

As will be described below, once the processing apparatus 16 has added all of the new data points 56 that are necessary or desired between pairs of data points 46, the processing apparatus is configured to compute an alpha shell of either the new data points 56 or a combination of the data points 46 and the new data points 56 to update the alpha shell 50, and therefore, the surface model of the anatomic structure.

While the different techniques for adding additional data points (e.g., new data points 56 and/or refined data points 60) to the point cloud 48 have been primarily described above as separate and distinct or independent techniques, it will be appreciated that in practice the techniques may be employed alone, or two or more techniques may be used in concert. Accordingly, embodiments wherein the processing apparatus 16 employs two or more of the above described techniques remain within the spirit and scope of the present disclosure.

Regardless of which technique(s) are used to add additional data points (e.g., new data points 56 and/or refined data points 60) to the point cloud 48, the processing apparatus 16 is further configured to update the alpha shell 50 using the new data points 56 and/or the refined data points 60, if applicable. More particularly, in one embodiment, the processing apparatus 16 is configured to compute a new surface model using only the new data points 56. In such an embodiment, the processing apparatus 16 is configured to compute a new surface model using an alpha shape algorithm to compute an alpha shell, and therefore surface model, of the new data points 56. In such an embodiment, the same value of alpha used to compute the alpha shell 50 may be used to compute the alpha shell of the new data points 50 (although the present disclosure is not meant to be so limited). The computation of the alpha shell of the new data points 56 results in the updating of the alpha shell 50 and serves to correct some or all of the defects (e.g., holes or other erroneous topology) in the original alpha shell 50.

In another exemplary embodiment, the processing apparatus 16 is configured to compute a new surface model using the original data points 46, as well as any additional data points added to the point cloud 48, such as new data points 56 and/or refined data points 60. As with the embodiment described above, in this embodiment the processing apparatus 16 is configured to use an alpha shape algorithm to compute a new alpha shell of the geometric structure, and may use the same value of alpha used to compute the alpha shell 50 in doing so (although the present disclosure is not meant to be so limited). The computing of the new alpha shell results in the updating of the alpha shell 50 and serves to correct some or all of the defects (e.g., holes or other erroneous topology) in the original alpha shell 50.

It will be appreciated that while the description above is primarily directed to an embodiment wherein the model construction system 14 is configured to repair or correct defects as part of an overall surface model generation process, the present disclosure is not meant to be so limited. Rather, in another exemplary embodiment, using the techniques described above, the model construction system 14 may be alternatively or additionally configured to repair previously generated surface models that may have been generated at a previous time or by other model construction systems. Accordingly, in such an embodiment, the model construction system 14 need not necessarily be configured to perform all of the surface model generation functionality (e.g., location point collection, generation of the original surface model/ alpha shell, etc.), but instead may be configured solely for post-processing of previously generated surface models that contain defects such as those described above.

It will be appreciated that in addition to the structure of the system 10 described above, another aspect of the present disclosure is a method for generating and/or repairing a surface model of a geometric structure. In an exemplary embodiment, and as described above, the model construction system 14 of the system 10, and the processing apparatus 16 thereof, in particular, is configured to perform the methodology. However, in other exemplary embodiments, the processing apparatus 16 is configured to perform some, but not all, of the methodology. In such an embodiment, another component or components that is/are part of the system 10 or that is/are configured for communication with the system 10, and the processing apparatus 16 thereof, in particular, is/are configured to perform some of the methodology.

Figure 15:
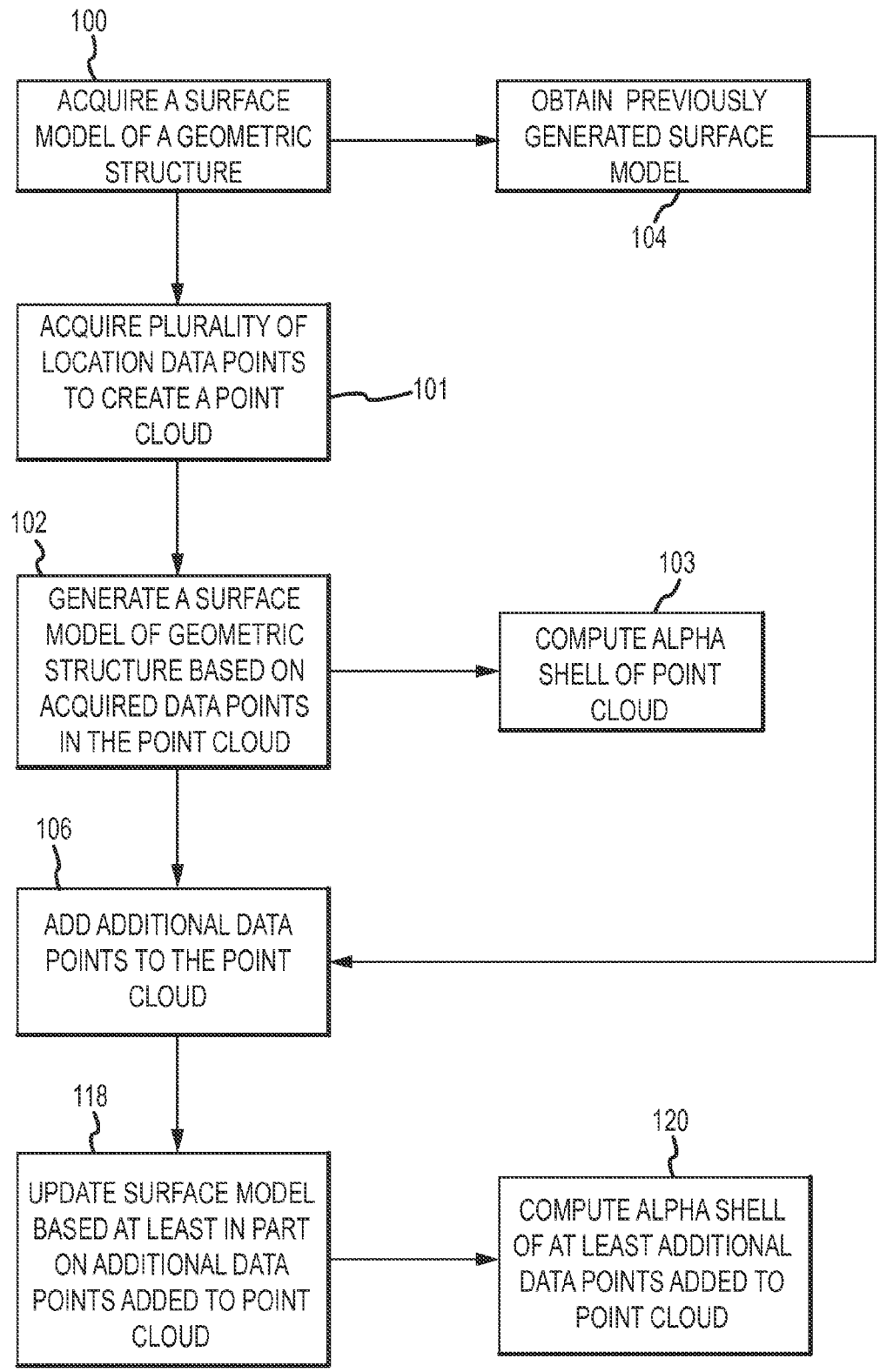
FIG. 15 is a flow chart illustrating methods for generating and/or repairing a surface model of a geometric structure in accordance with the present teachings.

In either instance, and with reference to FIG. 15, in an exemplary embodiment the method in its most general form includes a step 100 of acquiring a surface model of a geometric structure that is based on a plurality of location data points 46 corresponding to respective locations on the surface of the geometric structure, such as, for example, an anatomic structure, that collectively form a point cloud 48.

In an exemplary embodiment, the acquiring step 100 comprises a substep 101 of acquiring the plurality of location data points 46, and a substep 102 of generating a surface model of the anatomic structure based on the plurality of data points 46 of the point cloud 48. In an exemplary embodiment, step 102 comprises the substep 103 of generating the surface model by computing an alpha shell 50 of the point cloud 48 using an alpha shape algorithm. In another exemplary embodiment, the step 100 comprises a substep 104 of obtaining a previously generated surface model.

Figure 16:
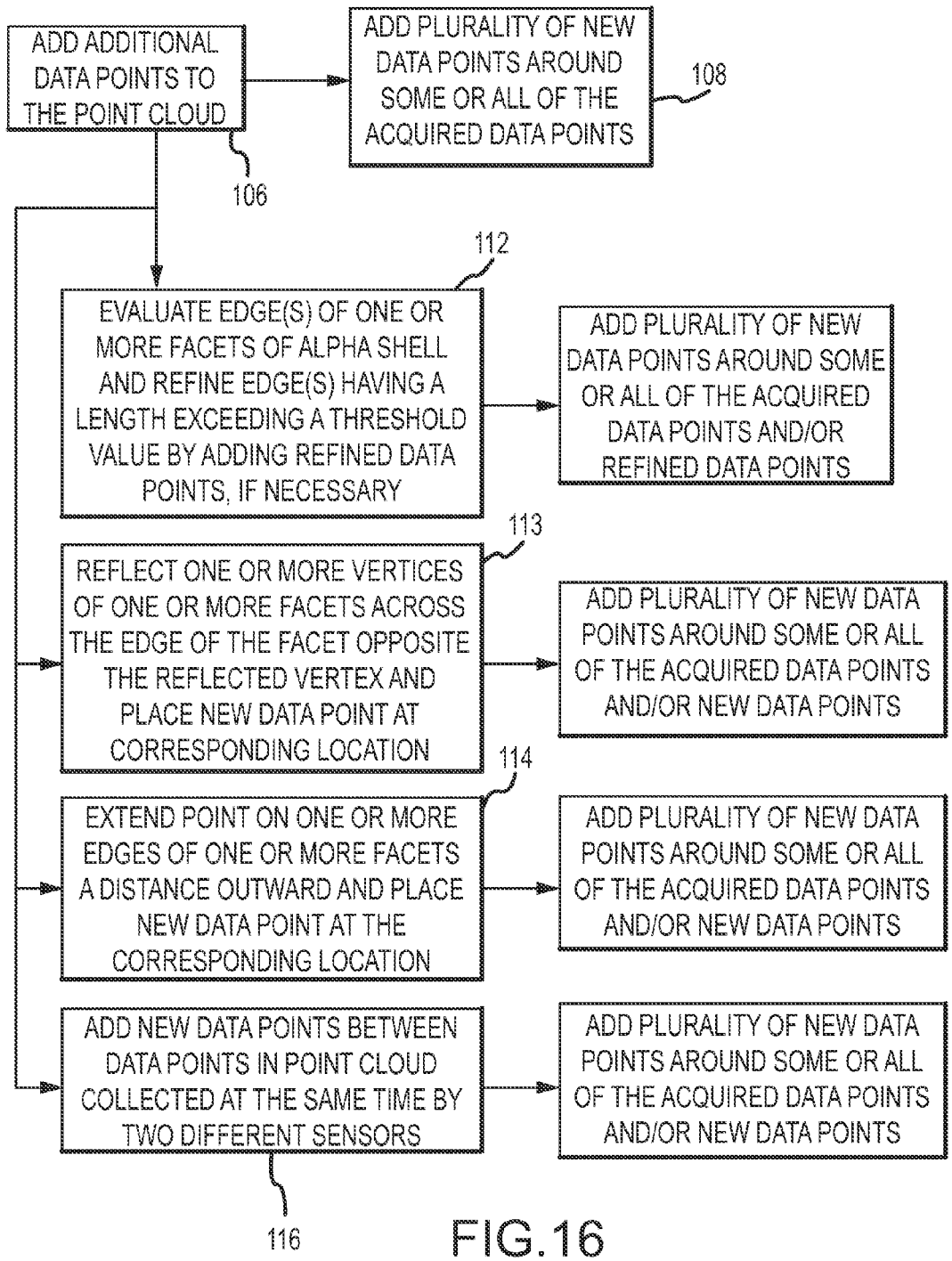
FIG. 16 is a flow chart illustrating exemplary embodiments of substeps of a data point adding step of the method illustrated in FIG. 15.

With reference to FIGS. 15-16, the method further comprises a step 106 of adding a plurality of additional data points (e.g., new data points 56 and/or refined data points 60) to the point cloud 48. In one exemplary embodiment, step 106 comprises a substep 108 of adding a plurality of new data points 56 near some or all of the data points 46 of the point cloud 48. More particularly, in an exemplary embodiment, substep 108 comprises centering a geometric shape on one or more of the data points 46, and adding new data points 56 to the point cloud 48 at each vertex of the geometric shape.

Figure 17:
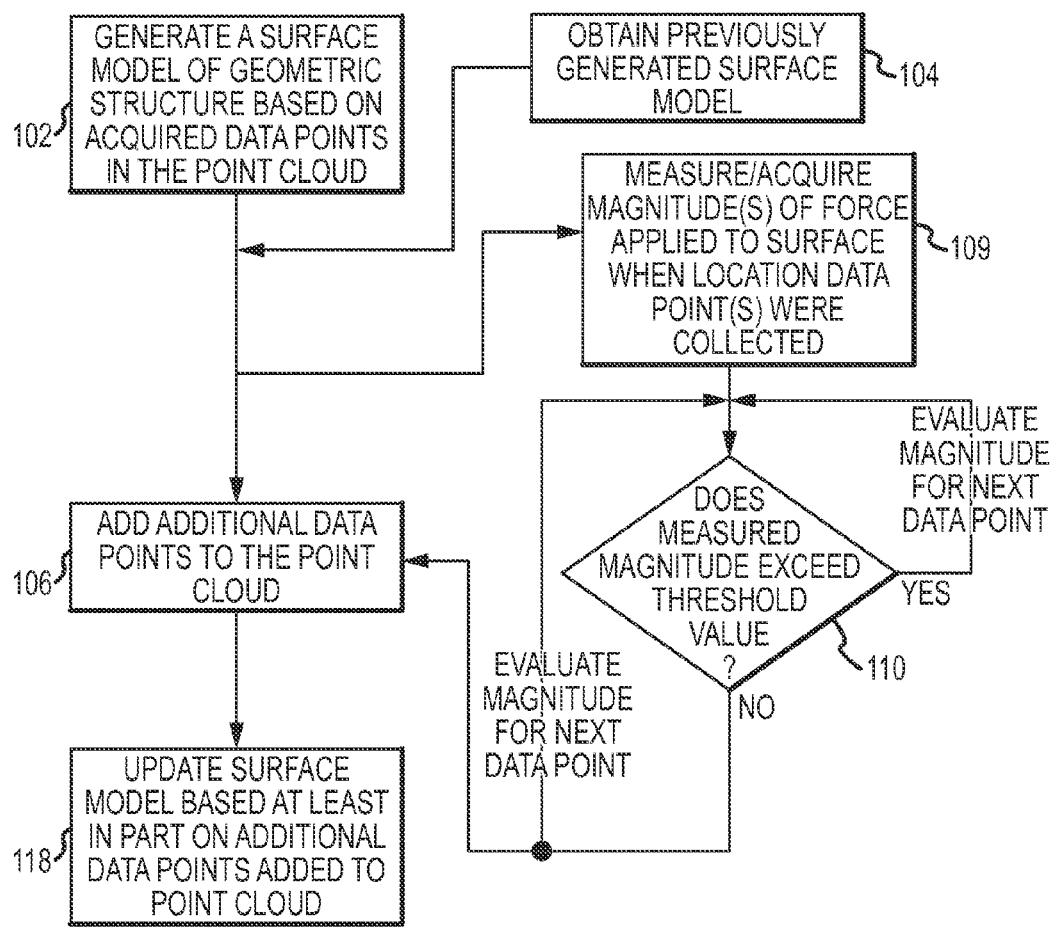
FIG. 17 is a flow chart illustrating intermediate steps of an exemplary embodiment of the method illustrated in FIG. 15.

In an exemplary embodiment such as, for example, that illustrated in FIG. 17, the method further comprises a step 109 of measuring or acquiring a magnitude of the force/pressure applied by the catheter when some or all of the data points 46 were collected, and a step 110 of comparing the measured/ acquired force/pressure magnitudes corresponding to some or all of the data points 46 with a predetermined threshold value. In an exemplary embodiment, the steps 109 and 110 are performed prior to the performance of the step 106 such that if the force/pressure magnitude for a given data point 46 exceeds (or, in an exemplary embodiment, meets or exceeds) the predetermined threshold value, the step 106 is not performed for that data point 46, but rather the step 110 is repeated for the next data point 46 in the point cloud for which new data points 56 may be added. Alternatively, the step 106 may be performed, but the number of new data points 56 that are added may be limited, and then step 110 is repeated for the next data point 46. Conversely, if the force/pressure magnitude falls below (or, in an exemplary embodiment, meets or falls below) the predetermined threshold, the step 106 may be performed for that particular data 46, and then step 110 may be repeated for the next data point 46 for which new data points 56 may be added.

In another exemplary embodiment, the step 106 comprises the substep 112 of evaluating one or more edges 53 of some or all of the facets 52 of the alpha shell 50 to determine if any edges 53 have lengths that exceed a predetermined threshold value, and refining those edges 53 found to exceed the threshold by creating, and adding to the point cloud 48, one or more refined data points 60.

The refining portion of substep 112 may take a number of forms. For example, in one embodiment those edges 53 requiring refinement are segmented whereby the edge 53 is divided into a plurality of segments, each of which has a length that is within the threshold value. The number of segments is dependent upon the length of the edge and the predetermined threshold value. The number of revised data points 60 that are added as a result of the segmentation process is dependent upon the number of segments into which the edge is divided. More particularly, the number of refined data points 60 that are added to an edge is one less than the number of segments into which the edge is divided. In another embodiment, rather than segmenting those edges 53 having lengths in excess of the threshold value, the facets 52 of which the edges 53 are a part are divided into four new facets. More particularly, a refined data point 60 is added to each edge 53 of a facet 52 containing an edge 53 having a length that exceeds the threshold value, and those refined data points 60 are triangulated to form four new facets 52. In an exemplary embodiment, the refined data points 60 are placed at the midpoint of each edge 53 of the facet 52. Each edge 53 of each new facet is then evaluated in the same manner described above. The process repeats itself until every relevant edge 53 in the alpha shell 50 has a length equal to or less than the threshold value. In either of the aforedescribed embodiments, the substep 112 may further comprise adding a plurality of new data points 56 near some or all of the data points 46 and/or refined data points 60 in the manner described above with respect to substep 108.

In another exemplary embodiment, the step 106 comprises the substep 113 of reflecting one or more data points 46/vertices of one or more of the facets 52, across the edge 53 of the respective facet 52 opposite the data point 46 or vertex being reflected. Substep 113 further comprises placing a new data point 56 in the same plane as the facet 52 at each location corresponding to the reflected data point 46 or vertex. In an exemplary embodiment, substep 113 may further comprise adding a plurality of additional new data points 56 near some or all of the data points 46 and/or new data points 56 in the manner described above with respect to substep 108.

In yet another exemplary embodiment, the step 106 comprises a substep 114 of extending a point on one or more edges 53 of one or more facets outward a predetermined distance. Substep 114 further comprises placing a new data point 56 in the same plane as the facet 52 at each location corresponding to the distance from the respective edge 53. In an exemplary embodiment, substep 113 may further comprise adding a plurality of additional new data points 56 near some or all of the data points 46 and/or new data points 56 in the manner described above with respect to substep 108.

In yet still another exemplary embodiment, the step 106 comprises a substep 116 of using the known configuration of the catheter 12 to add new data points 56 to the point cloud 48. More particularly, in an embodiment wherein a plurality of sensors 32 are used to collect data points 46, the spacing or locations of the sensors 32 on the shaft 26 of the catheter 12 relative to each other are known. Accordingly, when data points 46 are collected by and for each of the plurality of sensors 32 at the same or substantially same point in time, new data points 56 may be added in the space(s) between the plurality of sensors 32. As with substeps 112, 113 and 114 above, in an exemplary embodiment substep 116 may further comprise adding a plurality of additional new data points 56 near some or all of the data points 46 and/or new data points 56 in the manner described above with respect to substep 108.

In an exemplary embodiment, the method further comprises a step 118 of updating the previously generated surface model/alpha shell 50 based on at least some of the additional data points (e.g., new data points 56 and/or refined data points 60) added to the point cloud 48. In an exemplary embodiment, step 118 comprises the substep 120 of computing an alpha shell for only the data points added to the point cloud 48 in step 106. The resulting alpha shell comprises an updated surface model/alpha shell 50. In another exemplary embodiment, substep 120 comprises computing an alpha shell for both the original data points 46 and the added additional data points (e.g., new data points 56 and/or refined data points 60). The new computed alpha shell results in the creation of an updated surface model/alpha shell 50.

It will be appreciated that additional functionality described in greater detail above with respect to the system 10, and the model construction system 14 and processing apparatus 16, thereof, in particular, may also be part of the inventive methodology. Therefore, to the extent such functionality has not been expressly described with respect to the methodology, the description thereof above is incorporated herein by reference.

It should be understood that the model construction system 14, and particularly the processing apparatus 16, as described above may include conventional processing apparatus known in the art, capable of executing pre-programmed instructions stored in an associated memory, all performing in accordance with the functionality described herein. It is contemplated that the methods described herein, including without limitation the method steps of embodiments of the invention, will be programmed in a preferred embodiment, with the resulting software being stored in an associated memory and where so described, may also constitute the means for performing such methods. Implementation of the invention, in software, in view of the foregoing enabling description, would require no more than routine application of programming skills by one of ordinary skill in the art. Such a system may further be of the type having both ROM, RAM, a combination of non-volatile and volatile (modifiable) memory so that the software can be stored and yet allow storage and processing of dynamically produced data and/or signals.

Although only certain embodiments have been described above with a certain degree of particularity, those skilled in the art could make numerous alterations to the disclosed embodiments without departing from the scope of this disclosure. Joinder references (e.g., attached, coupled, connected, and the like) are to be construed broadly and may include intermediate members between a connection of elements and relative movement between elements. As such, joinder references do not necessarily infer that two elements are directly connected/coupled and in fixed relation to each other. Additionally, the terms electrically connected and in communication are meant to be construed broadly to encompass both wired and wireless connections and communications. It is intended that all matter contained in the above description or shown in the accompanying drawings shall be interpreted as illustrative only and not limiting. Changes in detail or structure may be made without departing from the invention as defined in the appended claims.

What is claimed is:

1. A method for generating a surface model of an anatomic structure, the method comprising:
   receiving, from a first sensor and a second sensor of a catheter, a plurality of location data points corresponding to respective locations on the surface of said anatomic structure, said plurality of location data points forming a point cloud;
   generating a first surface model of said anatomic structure based on said plurality of location data points;
   adding a plurality of additional data points to said point cloud, wherein said adding a plurality of additional data points to said point cloud comprises:
      creating a first subset of said plurality of additional data points around a first one of said location data points that are each a first predetermined distance from said first one of said location data points;
      creating a second subset of said plurality of additional data points around a second one of said location data points that are each a second predetermined distance from said second one of said location data points; and
      adding additional points to at least one of:
         an area between a first of said plurality of location data points and a second of said plurality of location data points;
         an area beyond a first of said plurality of location data points; and
         an area beyond a second of said plurality of location data points;
   updating said first surface model by constructing a second surface model based on said plurality of additional data points; and
   displaying the surface model of the anatomic structure by causing at least a portion of said first surface model, at least a portion of said second surface model, or both a portion of said first surface model and a portion of said second surface model to be displayed for a user.

2. The method of claim 1, wherein said generating step comprises computing an alpha shell of said point cloud, and said updating step comprises constructing said second surface model by computing an alpha shell of said additional data points.

3. The method of claim 1, wherein:
   said first subset of additional data points correspond to vertices of a regular geometric shape centered around said first location data point; and
   said second subset of additional data points correspond to vertices of a regular geometric shape centered around said second location data point.

4. The method of claim 3, wherein said geometric shape has a radius equal to a radius of a catheter used to collect said plurality of location data points.

5. The method of claim 1, wherein said first surface model comprises a plurality of facets each having at least one edge, said adding step comprising the substeps of:
   evaluating said at least one edge of one of said facets to determine if said edge has a length that exceeds a predetermined threshold value; and
   if the length of said edge exceeds said predetermined threshold value, dividing said edge into a plurality of segments each having a length that is equal to or less than said predetermined threshold value, and adding at least one refined data point on said edge to define said plurality of segments.

6. The method of claim 5, wherein said adding step further comprises adding new data points corresponding to at least one vertex of a geometric shape centered around said at least one refined location data point.

7. The method of claim 1, wherein said first surface model comprises a plurality of triangularly-shaped facets each having a first, a second, and a third edge, said adding step comprising the substeps of:
   evaluating at least one of said first, second, and third edges of one of said facets to determine if said edge has a length that exceeds a predetermined threshold value;
   if the length of said edge exceeds said predetermined threshold value, breaking said facet into a plurality of new triangularly-shaped facets by adding at least one refined data point on each of said first, second, and third edges of said facet and triangulating said refined data points to create said plurality of new triangularly-shaped facets; and
   evaluating at least one of said plurality of new facets to determine if any edges thereof have lengths that exceed said predetermined threshold value.

8. The method of claim 7, wherein said adding step further comprises adding new data points corresponding to at least one vertex of a geometric shape centered around at least one of said refined data points.

9. The method of claim 1, wherein said first surface model comprises a plurality of triangularly-shaped facets each defined by a first, a second, and a third data point and a first, a second, and a third edge, said adding step comprising the substeps of:
   reflecting at least one of said first, second, and third data points of one of said facets across the one of said first, second and third edges of said facet that is opposite said data point being reflected; and
   placing a new data point at the location where said reflected data point is disposed.

10. The method of claim 1, wherein said first surface model comprises a plurality of facets each having at least one edge, said adding step comprising the substeps of:
    extending a point on said at least one edge of one of said facets outwardly a predetermined distance from said edge; and
    placing a new data point at the location that is said predetermined distance form said at least one edge of said facet.

11. A system for generating a surface model of an anatomic structure, the system comprising:
    a processing apparatus configured to:
      receive, from a first sensor and a second sensor of a catheter, a plurality of location data points corresponding to respective locations on the surface of said anatomic structure, said plurality of location data points forming a point cloud;
      generate a first surface model of said anatomic structure based on said plurality of location data points;
      add a plurality of additional data points to said point cloud by adding the plurality of additional points to at least one of;
        an area between a first of said plurality of location data points and a second of said plurality of location data points;
        an area beyond a first of said plurality of location data points; and
        an area beyond a second of said plurality of location data points; and
      update said first surface model by constructing a second surface model based on said plurality of additional data points; wherein said first surface model comprises a plurality of facets each having at least one edge, said processing apparatus further configured to:
        evaluate said at least one edge of one of said facets to determine if said edge has a length that exceeds a predetermined threshold value;
        divide said edge into a plurality of segments, responsive to said evaluation, if said edge has a length that exceeds said predetermined threshold value, each of said segments having a length that is equal to or less than said predetermined threshold value; and
        add at least one refined data point on said edge to define said plurality of segments; and
      display the surface model of the anatomic structure by causing at least one of a portion of the first surface model and a portion of second surface model to be displayed for a user.

12. The system of claim 11, wherein said processing apparatus is configured to generate said model by computing an alpha shell of said point cloud, and to construct said second surface model by computing an alpha shell of said additional data points.

13. The system of claim 11, wherein said processing apparatus is configured to add additional data points to said point cloud by adding new data points corresponding to one or more vertices of a geometric shape centered around at least one of said plurality of location data points.

14. The system of claim 11, wherein said first surface model comprises a plurality of triangularly-shaped facets each having a first, a second, and a third edge, said processing apparatus configured to:
    evaluate at least one of said first, second, and third edges of one of said facets to determine if said edge has a length that exceeds a predetermined threshold value;
    break said facet into a plurality of new triangularly-shaped facets if said edge exceeds said predetermined threshold by adding at least one refined data point on each of said first, second, and third edges of said facet and triangulating said refined data points to create said plurality of new triangularly-shaped facets; and
    evaluate at least one of said plurality of new facets to determine if any edges thereof have lengths that exceed said predetermined threshold value.

15. The system of claim 11, wherein said first surface model comprises a plurality of triangularly-shaped facets each defined by a first, a second, and a third data point and a first, a second, and a third edge, said processing apparatus configured to:

reflect at least one of said first, second, and third data points of one of said facets across the one of said first, second and third edges of said facet that is opposite said data point being reflected; and place a new data point at the location where said reflected data point is disposed.

16. The system of claim 11, wherein said first surface model comprises a plurality of facets each having at least one edge, said processing apparatus configured to:

extend a point on said at least edge of one of said facets outwardly a predetermined distance from said edge; and place a new data point at the location that is said predetermined distance form said at least one edge of said facet.

17. A method of repairing a surface model of an anatomic structure, the method comprising:

acquiring said surface model of said anatomic structure, said model based on a plurality of location data points corresponding to respective locations on the surface of said anatomic structure, said location data points collectively forming a point cloud, wherein the plurality of location data points are received from a first sensor and a second sensor of a catheter;

adding a plurality of additional data points to said point cloud by adding the plurality of additional points to at least one of;

an area between a first of said plurality of location data points and a second of said plurality of location data points;

an area beyond a first of said plurality of location data points; and an area beyond a second of said plurality of location data points; and updating said surface model by constructing a second surface model based on said plurality of additional data points;

wherein said first surface model comprises a plurality of triangularly-shaped facets each defined by a first, a second, and a third data point and a first, a second, and a third edge, said method further comprising:

reflecting at least one of said first, second, and third data points of one of said facets across the one of said first, second and third edges of said facet that is opposite said data point being reflected; and placing a new data point at the location where said reflected data point is disposed; and displaying the surface model of the anatomic structure by causing at least a portion of said first surface model to be displayed for a user.

18. The method of claim 17, wherein said adding step comprises adding new data points corresponding to at least one vertex of a geometric shape centered around at least one of said plurality of location data points.

19. A method for generating a surface model of a geometric structure, the method comprising:

acquiring a plurality of location data points corresponding to respective locations on the surface of said geometric structure, said plurality of location data points forming a point cloud;

generating a first surface model of said geometric structure based on said plurality of location data points;

adding a plurality of additional data points to said point cloud wherein each of said additional data points is disposed a distance from at least one of said plurality of location data points that is equal to a radius of a catheter used to collect said plurality of location data points;

updating said first surface model by constructing a second surface model based on said plurality of additional data points; and causing at least a portion of said first surface model, at least a portion of said second surface model, or both a portion of said first surface model and a portion of said second surface model to be displayed for a user.

* * * * *